(12) United States Patent
Meade

(10) Patent No.: US 10,729,466 B2
(45) Date of Patent: Aug. 4, 2020

(54) UTERINE MANIPULATOR WITH CUTTING HEAD

(71) Applicant: Freyja Healthcare, LLC, North Andover, MA (US)

(72) Inventor: John C. Meade, North Andover, MA (US)

(73) Assignee: Freyja Healthcare, LLC, North Andover, MA (US)

( * ) Notice: Subject to any disclaimer, the term of this patent is extended or adjusted under 35 U.S.C. 154(b) by 0 days.

(21) Appl. No.: 16/368,457

(22) Filed: Mar. 28, 2019

(65) Prior Publication Data

US 2019/0216505 A1     Jul. 18, 2019

Related U.S. Application Data

(63) Continuation of application No. PCT/US2018/047402, filed on Aug. 21, 2018.
(Continued)

(51) Int. Cl.
*A61B 17/42* (2006.01)
*A61B 90/30* (2016.01)
(Continued)

(52) U.S. Cl.
CPC .... *A61B 17/4241* (2013.01); *A61B 17/00234* (2013.01); *A61B 18/1485* (2013.01);
(Continued)

(58) Field of Classification Search
CPC .......... A61B 17/4241; A61B 17/00234; A61B 90/30; A61B 2017/00557; A61B 2017/4225; A61B 17/32; A61B 17/320016; A61B 17/32002; A61B 17/320092; A61B 17/3203; A61B 17/3211; A61B 17/3213; A61B 17/320783; A61B 2017/320072; A61B 2017/320073; A61B 2017/320074; A61B 2017/320075; A61B 2017/32113;
(Continued)

(56) References Cited

U.S. PATENT DOCUMENTS

| | | |
|---|---|---|
| 670,231 A | 3/1901 | Heylman |
| 975,581 A | 11/1910 | Stevens |

(Continued)

FOREIGN PATENT DOCUMENTS

| | | |
|---|---|---|
| EP | 0229620 A2 | 7/1987 |
| RU | 2036669 C1 | 6/1995 |

(Continued)

OTHER PUBLICATIONS

PCT International Search Report and Written Opinion, PCT/US2012/065584, dated Feb. 14, 2013, 10 pages.
(Continued)

*Primary Examiner* — Kathleen S Holwerda
*Assistant Examiner* — Brooke Labranche
(74) *Attorney, Agent, or Firm* — Vista IP Law Group, LLP

(57) ABSTRACT

A uterine manipulator can include a shaft including a first end, a second end, and embodiments of a cutting head configured and arranged to receive a cervix. The cutting head can be configured and adapted to be used to cut the tissue joining the vaginal wall to the cervix and uterus to facilitate removal of the uterus in a minimally invasive manner.

19 Claims, 36 Drawing Sheets

Related U.S. Application Data

(60) Provisional application No. 62/548,252, filed on Aug. 21, 2017.

(51) Int. Cl.
    *A61B 18/14* (2006.01)
    *A61B 17/00* (2006.01)
    *A61B 17/34* (2006.01)
    *A61B 90/00* (2016.01)
    *A61B 18/00* (2006.01)
    *A61B 17/32* (2006.01)

(52) U.S. Cl.
    CPC ...... *A61B 90/30* (2016.02); *A61B 17/320016* (2013.01); *A61B 2017/00557* (2013.01); *A61B 2017/345* (2013.01); *A61B 2017/4225* (2013.01); *A61B 2018/00559* (2013.01); *A61B 2018/00601* (2013.01); *A61B 2018/144* (2013.01); *A61B 2090/036* (2016.02); *A61B 2090/306* (2016.02); *A61B 2090/309* (2016.02)

(58) Field of Classification Search
    CPC ....... A61B 2017/320097; A61B 2017/320095; A61B 2017/320094; A61B 2017/320093; A61B 2017/320077; A61B 10/0291; A61B 10/02; A61B 10/00; A61B 10/0233; A61B 10/0241; A61B 10/025; A61B 10/0266; A61B 10/0275; A61B 10/0283; A61B 2010/0208; A61F 9/00763
    See application file for complete search history.

(56) References Cited

U.S. PATENT DOCUMENTS

| | | |
|---|---|---|
| 998,038 A | 7/1911 | Ressler |
| 1,318,611 A | 10/1919 | Shaffer |
| 2,511,234 A | 6/1950 | Anderson |
| 2,759,261 A | 8/1956 | Setecka |
| 3,452,749 A | 7/1969 | Riedell |
| 3,948,259 A | 4/1976 | Bolduc et al. |
| 4,117,609 A | 10/1978 | Helt |
| 5,275,608 A | 1/1994 | Forman et al. |
| 5,314,445 A | 5/1994 | Heidmueller nee Degwitz et al. |
| 5,381,943 A | 1/1995 | Allen et al. |
| 5,409,496 A | 4/1995 | Rowden |
| 5,431,323 A | 7/1995 | Smith et al. |
| 5,487,377 A | 1/1996 | Smith et al. |
| 5,520,698 A | 5/1996 | Koh |
| 5,540,700 A | 7/1996 | Rowden |
| 5,643,285 A | 7/1997 | Rowden |
| 5,795,308 A | 8/1998 | Russin |
| 5,840,077 A | 11/1998 | Rowden |
| 5,906,579 A | 5/1999 | Vander |
| 6,030,406 A | 2/2000 | Davis |
| 6,059,719 A | 5/2000 | Yamamoto |
| 6,156,006 A | 12/2000 | Brosens |
| 6,230,593 B1 | 5/2001 | Hsieh |
| 6,331,166 B1 * | 12/2001 | Burbank ............ A61B 10/0266 600/567 |
| 6,464,711 B1 | 10/2002 | Emans et al. |
| 7,824,342 B2 | 11/2010 | Minosawa |
| 8,079,963 B2 | 12/2011 | Rosenblatt |
| 8,323,278 B2 | 12/2012 | Brecheen |
| 8,460,289 B2 * | 6/2013 | Sartor ............... A61B 18/1402 606/45 |
| 8,608,738 B2 | 12/2013 | Brecheen |
| 8,858,586 B2 | 10/2014 | Chang |
| 9,629,660 B2 | 4/2017 | Einarsson |
| 10,016,219 B2 | 7/2018 | Einarsson |
| 2001/0021854 A1 | 9/2001 | Donnez |
| 2008/0147113 A1 | 6/2008 | Nobis et al. |
| 2010/0228089 A1 | 9/2010 | Hoffman et al. |
| 2012/0209254 A1 | 8/2012 | Park et al. |
| 2012/0330324 A1 | 12/2012 | Sauer |
| 2013/0172918 A1 | 7/2013 | Smith |
| 2014/0012305 A1 | 1/2014 | Horton et al. |
| 2014/0180282 A1 | 6/2014 | Brecheen |
| 2014/0276812 A1 | 9/2014 | Batchelor et al. |
| 2014/0358158 A1 | 12/2014 | Einarsson |
| 2015/0250992 A1 | 9/2015 | Morriss |
| 2015/0351621 A1 | 12/2015 | Hill et al. |
| 2017/0156756 A1 | 6/2017 | Adajar |
| 2017/0189065 A1 | 7/2017 | Einarsson |
| 2017/0189066 A1 | 7/2017 | Parys et al. |
| 2018/0325552 A1 * | 11/2018 | Weihe ............... A61B 18/1482 |

FOREIGN PATENT DOCUMENTS

| | | |
|---|---|---|
| SU | 731961 A1 | 5/1980 |
| WO | 9611641 A1 | 4/1996 |
| WO | 2013115892 A1 | 8/2013 |
| WO | 2019040461 A1 | 2/2019 |
| WO | 2019040542 A1 | 2/2019 |

OTHER PUBLICATIONS

USPTO. PCT International Search Report and Written Opinion dated Oct. 24, 2018, for PCT/US2018/047272, 13 pages.

USPTO. PCT International Search Report and Written Opinion dated Dec. 11, 2018, for PCT/US2018/047402, 10 pages.

* cited by examiner

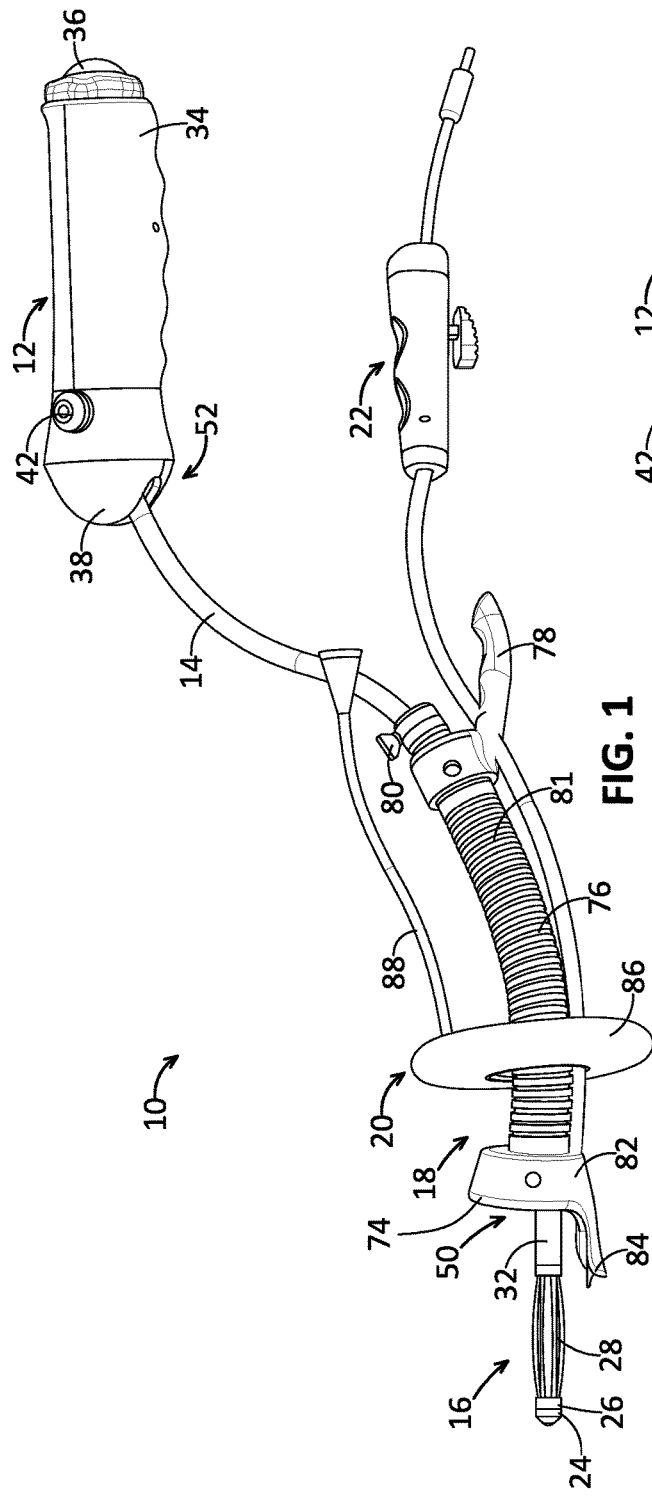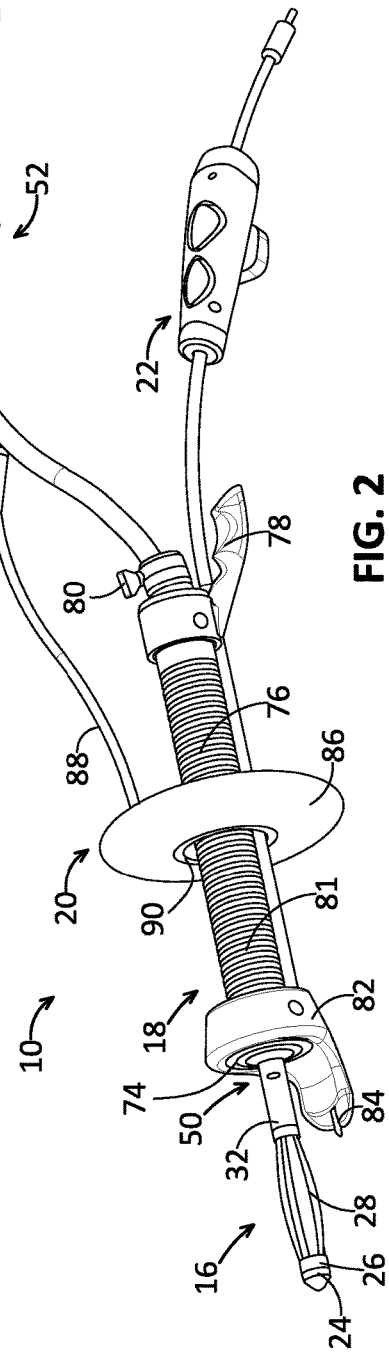
FIG. 1
FIG. 2

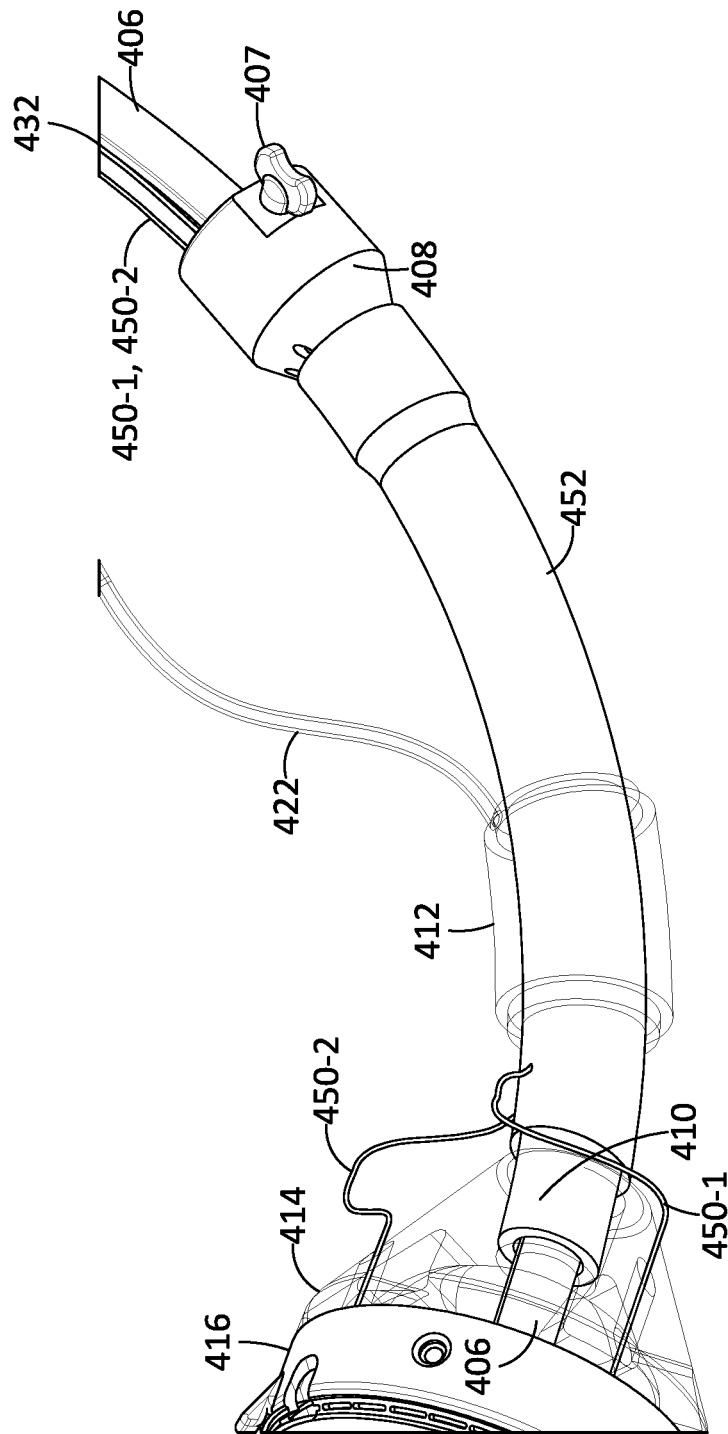

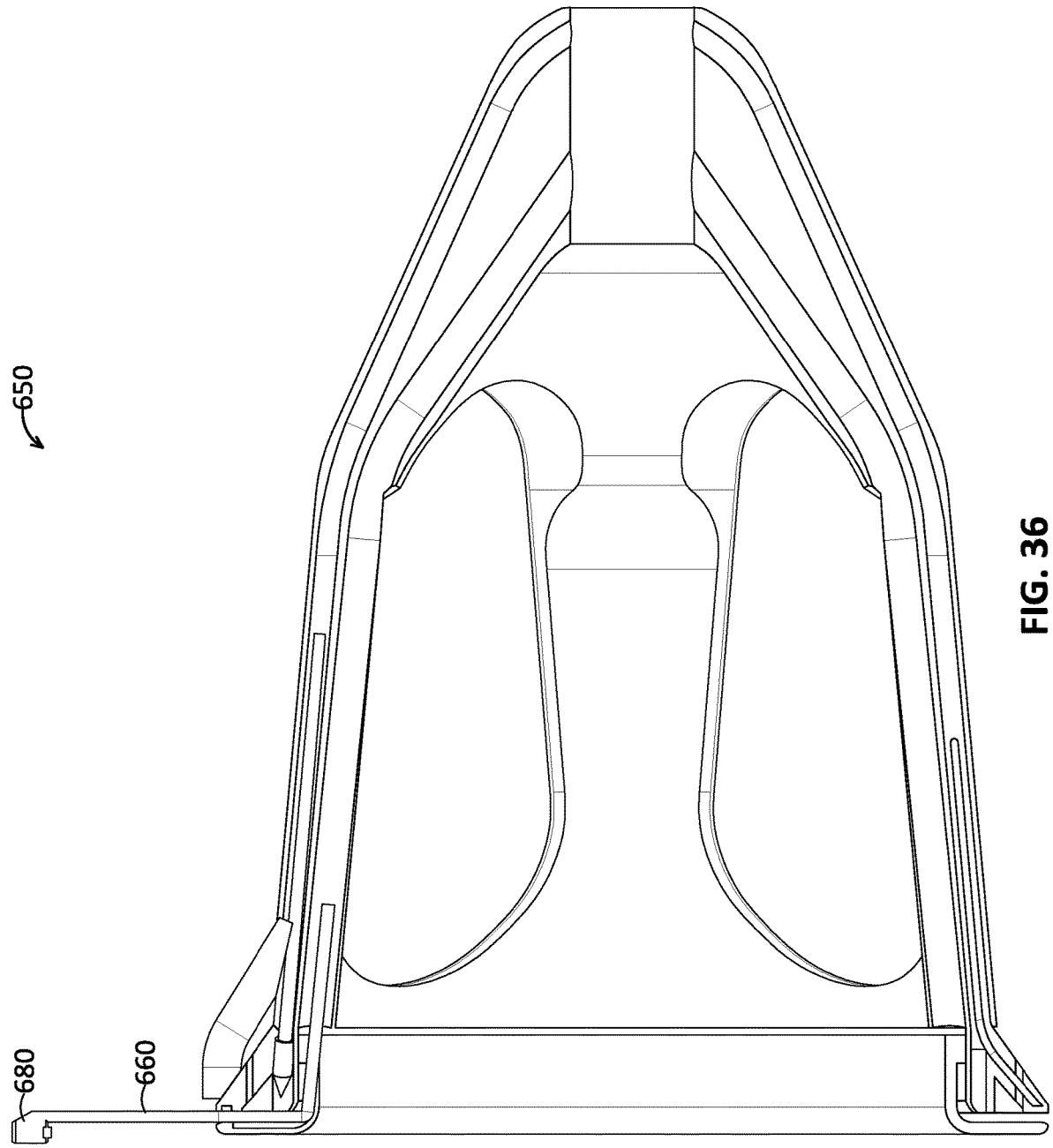

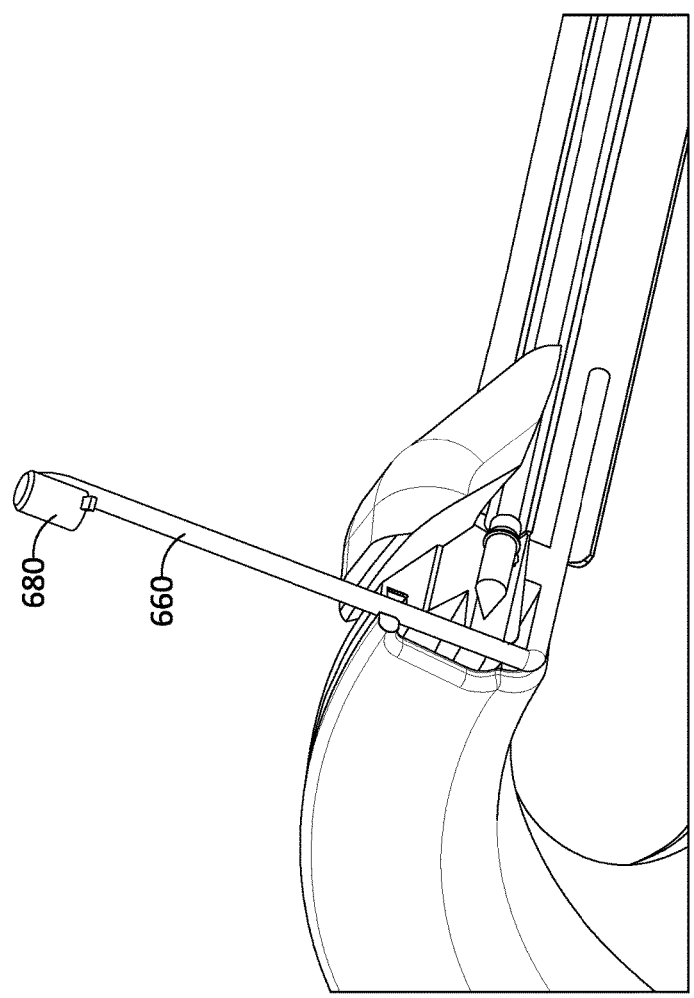
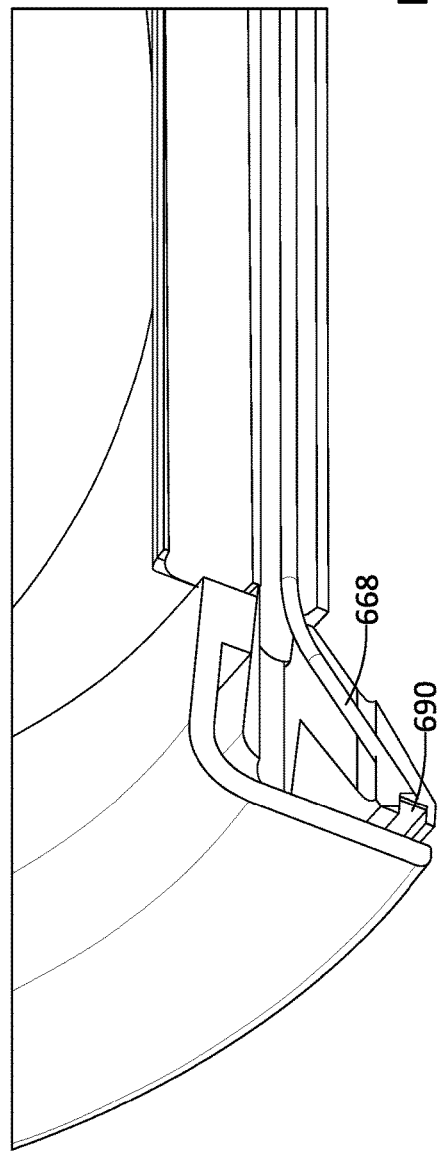

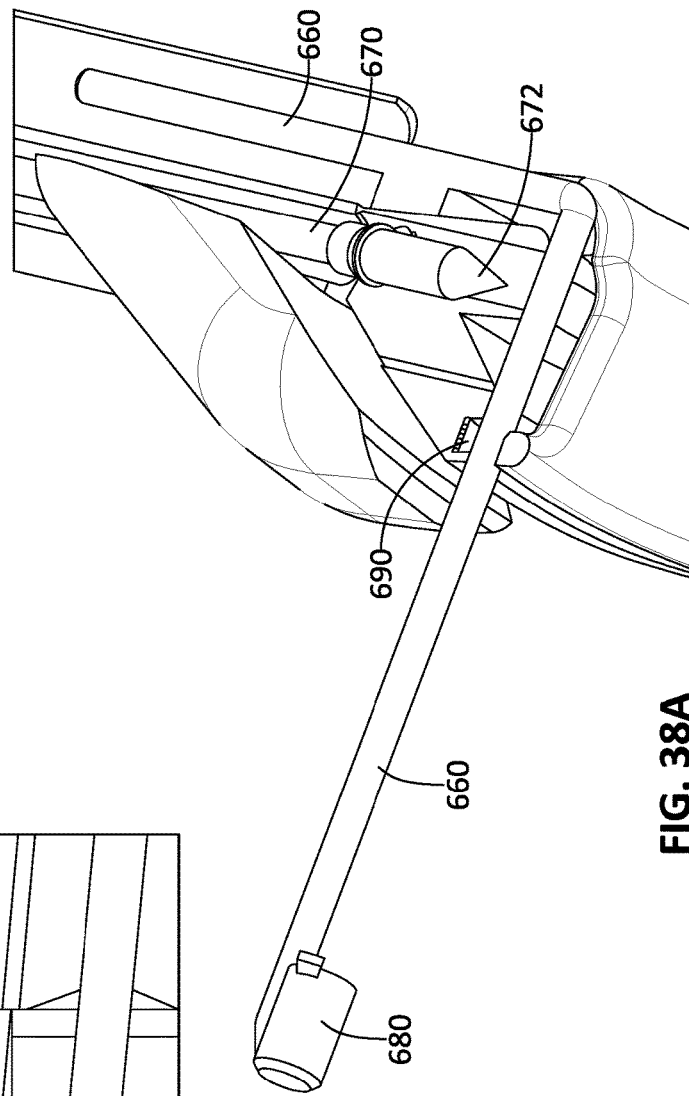
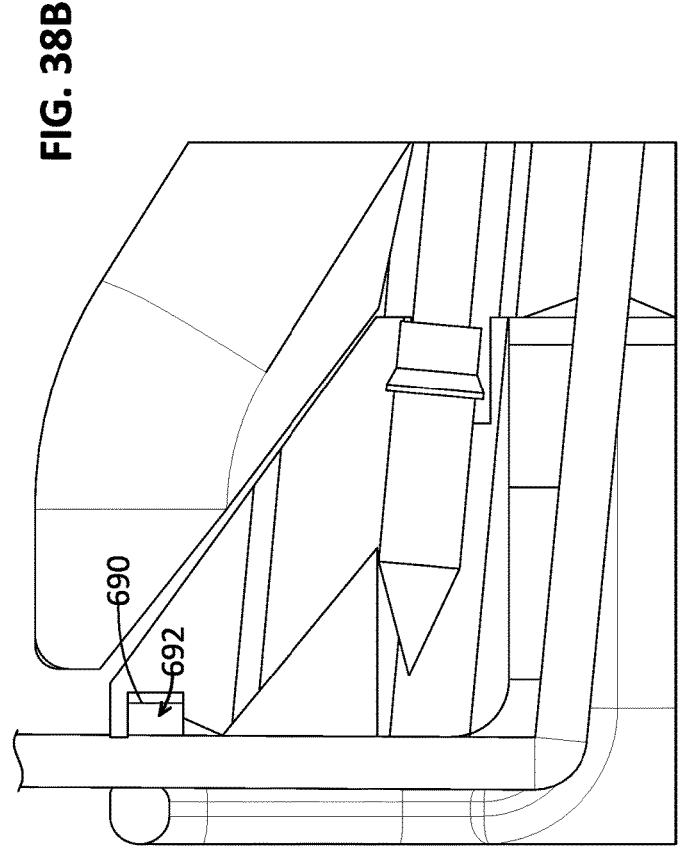
FIG. 38B
FIG. 38A

UTERINE MANIPULATOR WITH CUTTING HEAD

CROSS-REFERENCE TO RELATED APPLICATIONS

The present patent application is a continuation of and claims the benefit of priority to International Patent Application No. PCT/US2018/47402, filed Aug. 21, 2018, which in turn claims the benefit of priority to U.S. Provisional Patent Application No. 62/548,252, filed Aug. 21, 2017. Each of the foregoing patent applications is hereby incorporated by reference herein for any purpose whatsoever.

BACKGROUND

The present disclosure relates generally to uterine manipulators and methods of using a uterine manipulator. Uterine manipulators can be used, for example, as aids in laparoscopic hysterectomies.

SUMMARY

Embodiments of the present disclosure can be used to mobilize and position the uterus, to provide better visualization of the vagina and the cervix for facilitating their separation, and to remove the uterus after colpotomy is performed. An embodiment in accordance with the present disclosure can include a handle, a shaft, an inflatable balloon, and a cervical stop. The handle can be located at a proximal end of the shaft and the inflatable balloon can be located near the distal end of the shaft. The inflatable balloon can be maneuvered into the uterus in a deflated condition and then inflated (e.g., via saline or water injected through the shaft) to help stabilize the uterine manipulator during a procedure. The inflatable balloon can be used to remove the uterus after it has been separated from the vagina. Once the uterine manipulator is positioned, the cervical stop can be adjusted to abut the cervix.

Another embodiment of can include a handle, a shaft, an inflatable balloon, a cervical cup, and an occluder. The handle, the shaft, and the inflatable balloon can have similar functions as described above. The cervical cup can be fitted around the cervix and pressed inward against the vaginal fornix in order to provide an observable or palpable landmark of an incision point, such as that for dissecting the cervix and uterus from the vagina, and to physically separate the incision area from nearby ureters. An incision for detaching the uterus and cervix from the vagina can be executed laparoscopically (e.g., via a hook electrode). The occluder, positioned within the vagina when the uterine manipulator is set, can make continuous radial contact with the vaginal wall in order to maintain pneumoperitoneum after the incision between the vagina and the cervix has been made. The occluder can be a silicone cup pushed up the shaft and pressed into the vagina, or a balloon slid onto the shaft and inflated so that it presses against the vaginal wall.

In some embodiments, a uterine manipulator is provided that includes a shaft including a first end, a second end, and a channel along an axis of the shaft, a handle coupled to the first end of the shaft, and a triangular balloon coupled to the second end of the shaft, the triangular balloon being configured and arranged to match the shape of an inner portion of a uterus upon inflation, wherein the triangular balloon is in fluid communication with a fluid reservoir containing inflation fluid by way of the channel, the fluid reservoir being coupled to an actuator, and further wherein the triangular balloon is configured to be selectively inflated with fluid upon insertion into a uterus by actuating the actuator to cause the triangular balloon to conform to an inner surface of the uterus.

If desired, the proximal tip of the triangular balloon can be connected to the shaft, and the distal end of the triangular balloon can include two distal tips located at outward corners of the triangular balloon pointing along a direction that is generally perpendicular to a longitudinal axis of the shaft, wherein, upon inflation, the distal tips of the triangular balloon are sized and shaped to be located near the entrances to a patient's fallopian tubes. The two distal tips of the triangular balloon can each include at least one aperture in fluid communication with a channel that traverses the balloon to a fluid reservoir near the proximal end of the manipulator that includes dye fluid and an actuator, wherein actuating the actuator causes dye fluid to flow out of the balloon and toward the fallopian tubes of a patient when the triangular balloon is deployed. If desired, the inflation fluid can be the dye fluid and further wherein the fluid reservoir for the inflation fluid can be the same reservoir for containing the dye fluid. Alternatively, the inflation fluid and dye fluid can be two separate fluids in two separate fluid flow systems.

In some implementations, the two distal tips of the triangular balloon can each include at least one aperture in fluid communication with an interior portion of the triangular balloon, and further wherein the inflation fluid can include dye fluid, wherein actuating the actuator causes dye fluid to flow out of the balloon and toward the fallopian tubes of a patient when the triangular balloon is deployed. In some embodiments, the dye fluid can be suitable for use in a chromopertubation procedure. For example, the fluid can include at least one of methylene blue and indigo carmine.

In further implementations, the uterine manipulator can further include a light source coupled to the second end of the shaft configured to illuminate an interior volume of the uterus. For example, the light source is positioned internally with respect to the triangular balloon. The light source can include at least one LED, for example. If desired, the light source can include a plurality of LEDs operably coupled to a controller, the controller being configured to mix the colors of the LEDs to achieve a desired light output. In some embodiments, the plurality of LEDs can include LEDs having differing color output attributes. The controller can have a control circuit that is operable to tune the temperature of the light of the plurality of the LEDs to a desired temperature. If desired, the controller can be operable to tune the temperature of the light of the plurality of the LEDs to a desired color.

In some implementations, a method of diagnosing a medical condition is provided, including providing a uterine manipulator as set forth above, introducing the triangular balloon into the patient's uterus, and illuminating the light source to illuminate the patient's uterus. The method can further include viewing an inner surface of the uterus using an optic to examine the endometrial lining of the uterus. If desired, the method can include inspecting the patient's uterus externally to search for fibroids, wherein the light source is of sufficient intensity to illuminate the uterus internally.

If desired, the uterine manipulator can further include a channel coupled to the second end of the shaft and a corner of the triangular balloon, and positioned internal to the triangular balloon, the channel configured and arranged to inject the dye into an opening of a fallopian tube. The shaft can include a groove, and the uterine manipulator can further include a cup. The cup can include a projection that interfaces with the groove of the shaft and is configured to be positioned at a juncture between a cervix and the vagina. If desired, the uterine manipulator can further include a pneumooccluder coupled to the shaft, a first end of a filling tube coupled to a fluid inlet, and a second end of the filling end coupled to the pneumooccluder.

The disclosure further provides embodiments of a uterine manipulator. The uterine manipulator typically includes a shaft including a proximal end, a distal end, and a channel along a longitudinal axis of the shaft, a handle coupled to the proximal end of the shaft, and a cutting head attached to the distal end of the shaft adapted to cut a tissue segment to separate a vagina from a cervix and uterus. The cutting head typically includes a cup coupled to the distal end of the shaft and configured to be positioned at a juncture between the cervix and a vagina, and a cutting wire coupled to the cup via an aperture in the cup such that a portion of the cutting wire extends away from an exterior surface of the cup. The cutting wire is typically configured to follow a substantially circular path about the longitudinal axis of the shaft when cutting through tissue to separate the cervix from the vagina.

If desired, a system can be provided including the uterine manipulators described herein, and a power source coupled to the cutting wire to apply electrical current to a cutting wire portion of the uterine manipulator. The uterine manipulator and power source can be configured and arranged to provide monopolar current or bipolar current to a patient. A cup at a distal end of the uterine manipulator can be provided that includes a metal ring coupled thereto. The metal ring can be attached to a return path conductor that leads toward a proximal end of the uterine manipulator.

If desired, the cutting wire can be configured and arranged to traverse a circumference of the distal portion of the cup along a groove defined between a distal end cap of the cup and a proximal frame portion of the cup. The uterine manipulator can further include a push wire slidably disposed along the uterine manipulator, wherein a distal end portion of the push wire can be configured and arranged to carry a distal portion of the cutting wire outwardly from a distal end portion of the manipulator. The push wire can be configured to traverse an opening defined through an end cap of the distal end portion of the uterine manipulator. The cutting wire can be loaded into a distal end portion of the manipulator. Distal advancement of the push wire can carry the cutting wire distally and radially outward with respect to a distal end of the uterine manipulator.

The disclosure further provides methods of separating a uterus from a vagina of a patient. The methods typically include providing a uterine manipulator as described herein that include a cutting head, inserting a distal end portion of the uterine manipulator through a cervix of the patient, and deploying the cutting wire through the tissue of the vagina and/or cervix outwardly into an abdominal cavity of the patient.

If desired, a method can be provided that further includes visualizing the cutting wire in the abdominal cavity through a laparoscopic procedure including insufflating the abdominal cavity of the patient, and visually locating a portion of the cutting wire extending into the abdominal cavity. The method can further include grasping the cutting wire using a second surgical instrument from within the abdominal cavity, and pulling the wire circumferentially around the cervix to sever the uterus and/or cervix from the vagina. In some implementations, the cutting can be accomplished without application of electrical current to the uterine manipulator. In other embodiments, the cutting can be accomplished with application of electrical current to the uterine manipulator.

Some previous approaches may present drawbacks. Some previous approaches to intrauterine balloons do not conform to the uterine cavity and therefore do not offer optimal mobilization of the uterus. Further, while some previous approaches offer chromopertubation, the dye is injected from the tip of the manipulator and may be inadvertently injected into the uterine muscle, which may affect fertility. Also, entry into the uterine cavity during a myomectomy is not easily detected with some previous approaches. In addition, some previous approaches may only serve to provide guidance for detaching the uterus and the cervix from the vagina via laparoscopic tools.

At least one embodiment in accordance with the present disclosure overcomes these drawbacks.

BRIEF DESCRIPTION OF THE DRAWINGS

FIG. 1 is a perspective view of a uterine manipulator according to the present disclosure.

FIG. 2 is another perspective view of the uterine manipulator of FIG. 1.

FIG. 22 illustrates a distal portion of the uterine manipulator of FIG. 16.

FIG. 36 is a side section view of the distal end portion of the uterine manipulator presented in FIG. 26A with the hot lead fully deployed and positioned to cut through tissue to separate a cervix and uterus from a vaginal wall.

FIG. 37A is an isometric close up section view of the distal end portion of the uterine manipulator presented in FIG. 26A with the hot lead fully deployed and positioned to cut through tissue to separate a cervix and uterus from a vaginal wall.

FIG. 37B is an isometric close up section view of the distal end portion of the uterine manipulator presented in FIG. 26A showing a portion opposite the hot lead, illustrating a portion of a conductive ring connected to a further electrical conductor for providing a return path for applied power.

FIG. 38A is a further isometric close up section view of the distal end portion of the uterine manipulator presented in FIG. 26A with the hot lead fully deployed and positioned to cut through tissue to separate a cervix and uterus from a vaginal wall.

FIG. 38B is a side close up sectional view of a distal end portion of the uterine manipulator presented in FIG. 26A with the hot lead fully deployed and positioned to cut through tissue to separate a cervix and uterus from a vaginal wall, specifically illustrating a portion of a ring-shaped, or toroidal gap defined between the hot lead and a conductive ring attached to a return conductor.

DETAILED DESCRIPTION

Figure 12A:
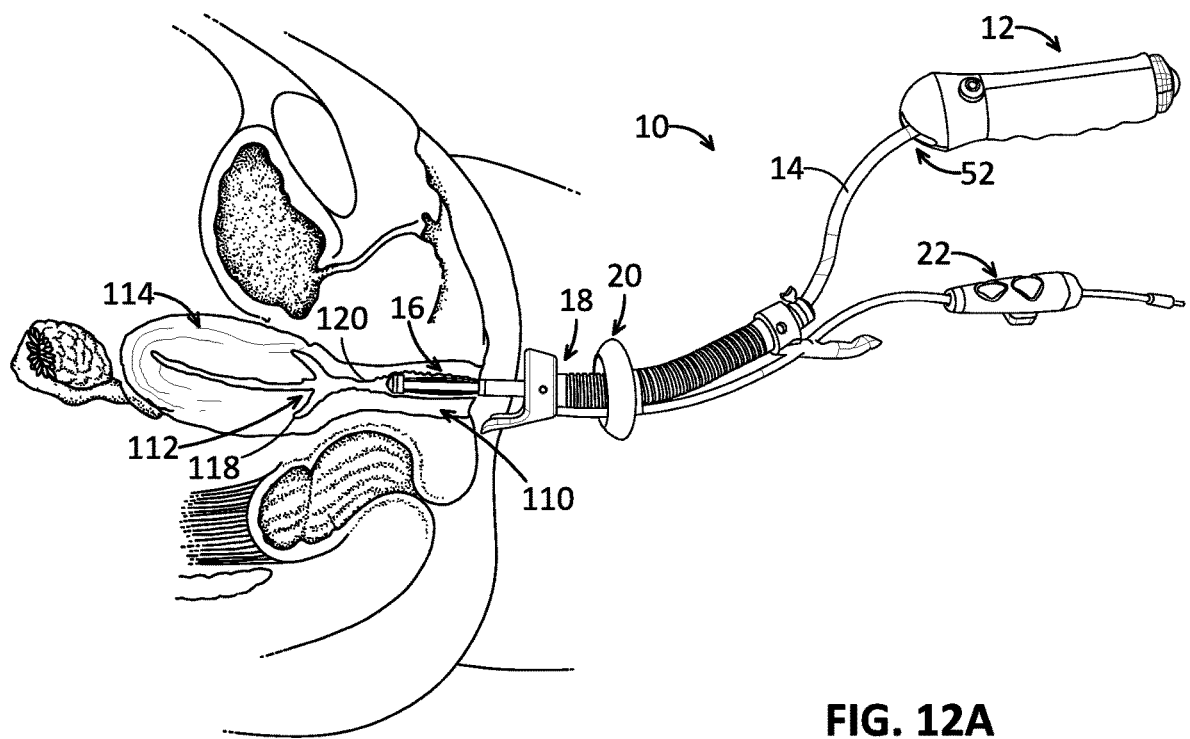
FIGS. 12A-12D are cross-sectional views of a pelvic cavity and the uterine manipulator of FIG. 1.
Figure 12B:
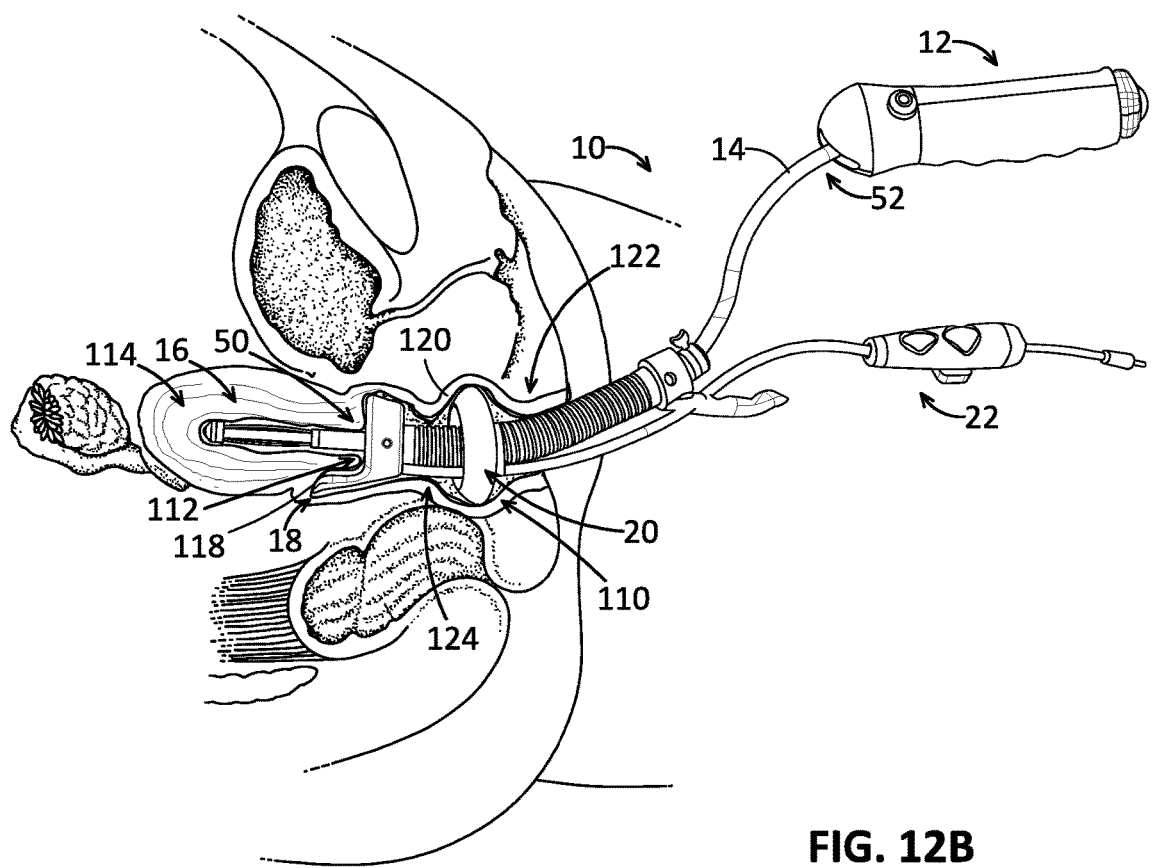
Figure 12C:
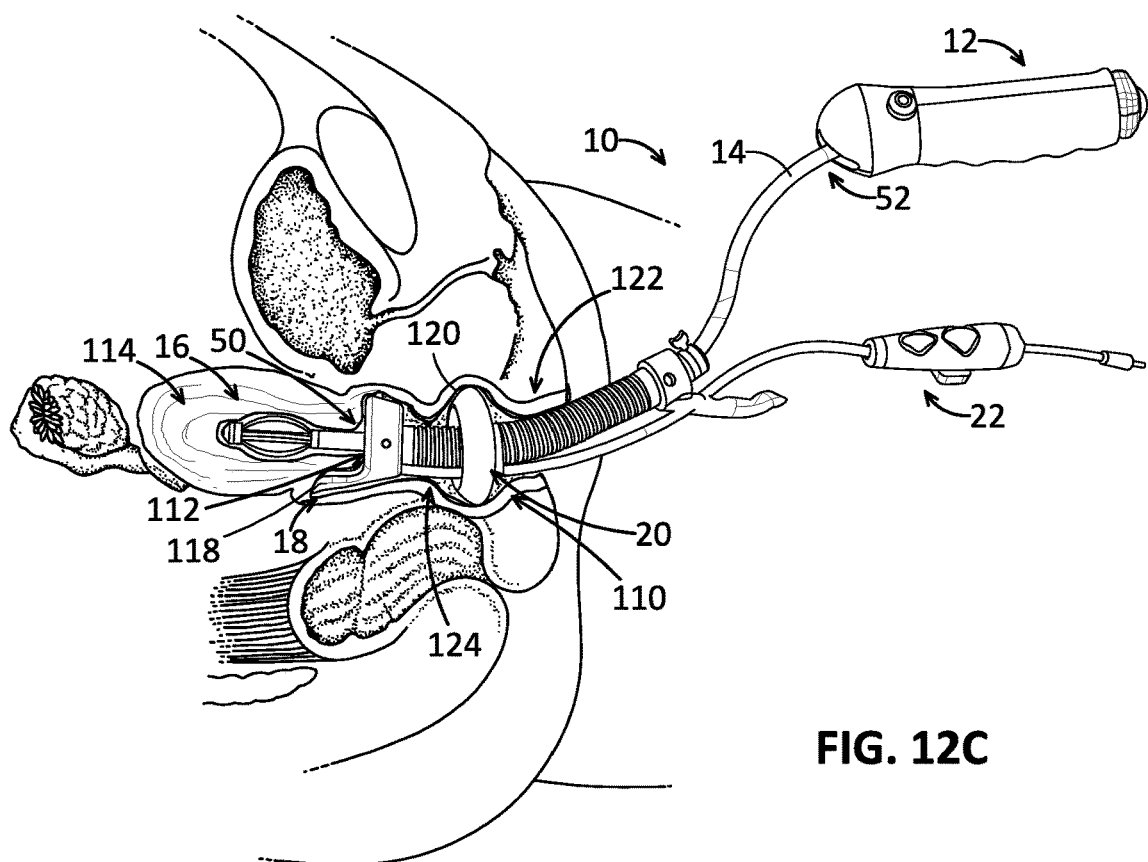

FIGS. 1 and 2 illustrate a uterine manipulator according to the present disclosure. At least one embodiment can be used in laparoscopic hysterectomies, robotic hysterectomies, laparoscopic myomectomies, and/or other pelvic procedures. The uterine manipulator 10 can include a handle 12, a shaft 14, a tip assembly 16, a cutting assembly 18, a pneumooccluder 20, and an electrical connector assembly 22. During use, the uterine manipulator 10 can be inserted into a patient's vagina 110, as shown in FIG. 12A, and then guided past the cervix 112 and into the uterus 114, as shown in FIG. 12B, using the handle 12. As shown in FIGS. 12B and 12C, when the uterine manipulator 10 is inserted, the tip assembly 16 can be positioned in the uterus 114, the cutting assembly 18 can be positioned adjacent to the vaginal fornix 118 and can press against the cervix 112, and the pneumooccluder 20 can be positioned inside the vagina 110.

Figure 3:
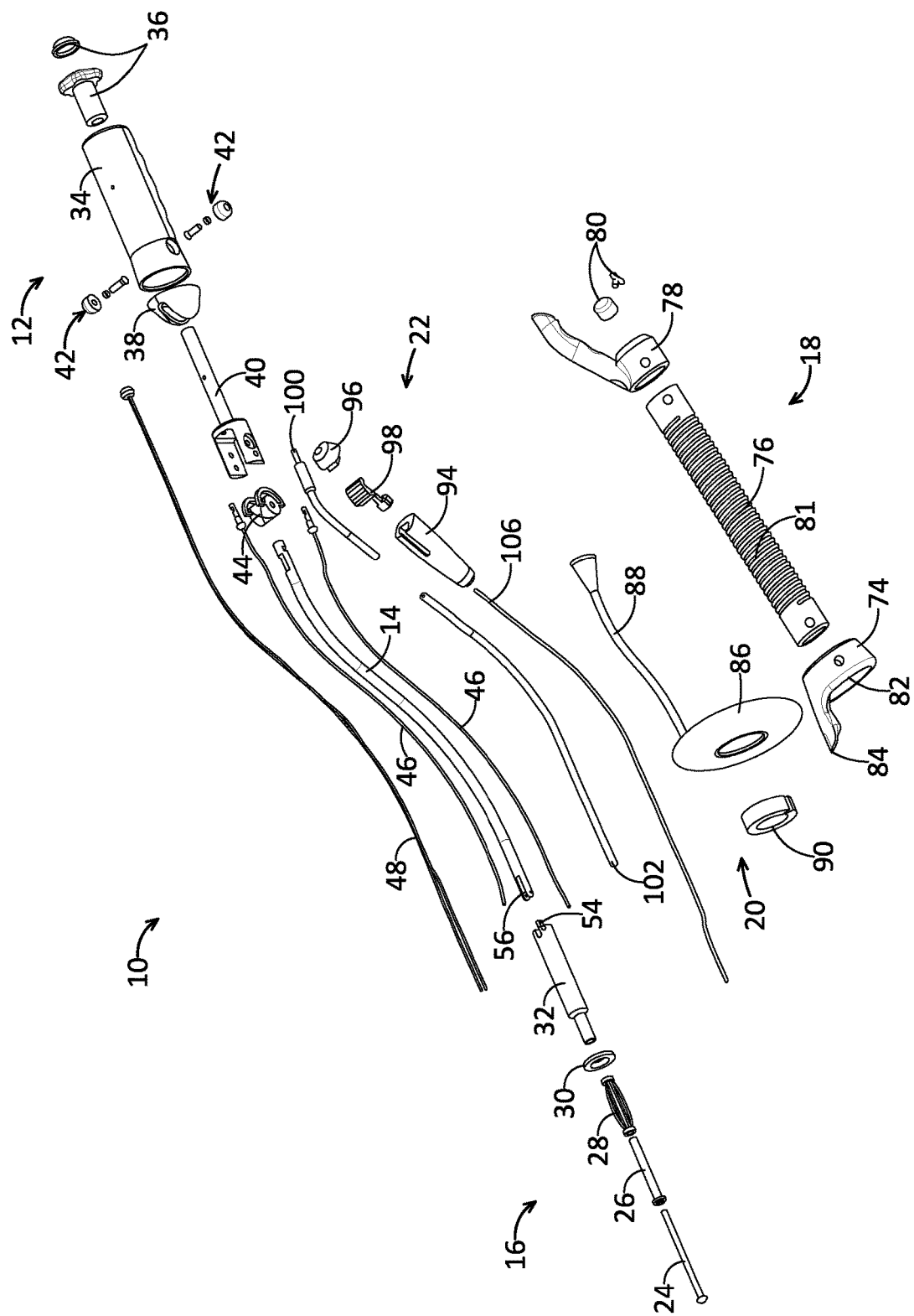
FIG. 3 is an exploded perspective view of the uterine manipulator of FIG. 1.
Figure 4A:
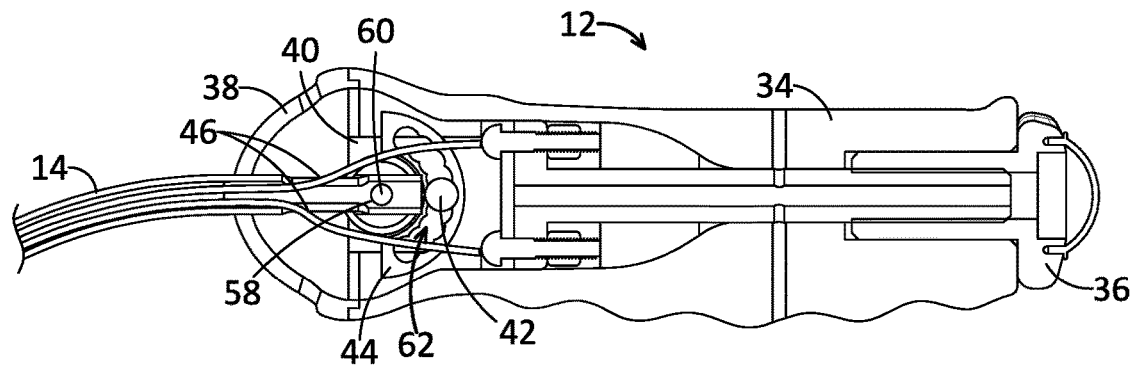
FIGS. 4A and 4B are partial side views of a handle and a tip assembly, respectively, of the uterine manipulator of FIG. 1.
Figure 4B:
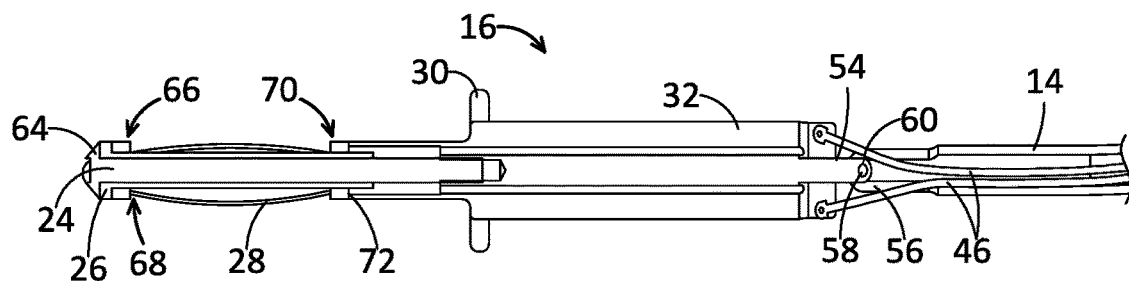
Figure 5A:
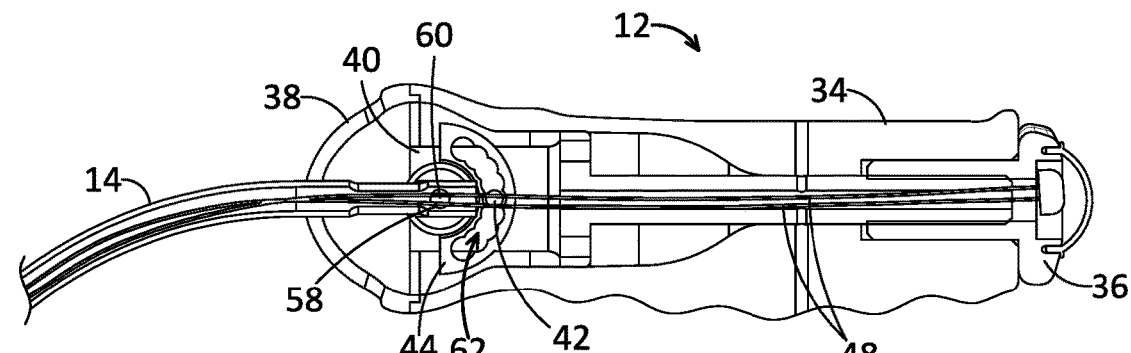
FIGS. 5A and 5B are additional partial side views of the handle and the tip assembly, respectively, of the uterine manipulator of FIG. 1.
Figure 5B:
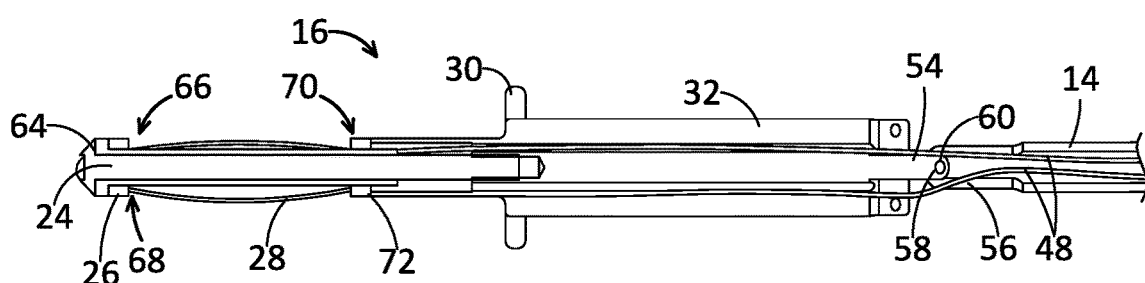

As shown in FIG. 3, the tip assembly 16 can include an expansion tip 24, a tip shaft 26, expansion elements 28, an abutment 30, and a tip housing 32, and the handle 12 can include a handle housing 34, an expansion actuator 36, a cap 38, a hinge 40, hinge pins 42, and a pivoting element 44. The shaft 14 can be coupled to the tip assembly 16 via the tip housing 32, and can be coupled to the handle 12 via the pivoting element 44. The tip assembly 16 can be coupled to the handle 12 via connectors 46. As shown in FIGS. 4A and 4B, the connectors 46 can be routed from inside the handle housing 34, through the shaft 14, and coupled to the tip housing 32. As shown in FIGS. 3, 5A and 5B, expansion connectors 48 can be coupled to the expansion actuator 36, routed from inside the handle housing 34 through the shaft 14 and coupled to the expansion tip 24 for actuating the tip assembly 16, as further described below. In at least one embodiment, some or all of the components of the uterine manipulator 10 can be disposable. Some or all of the components can be removable from one another, for example, so that disposable components can be uncoupled from permanent components and replaced with new disposable components.

Figure 6A:
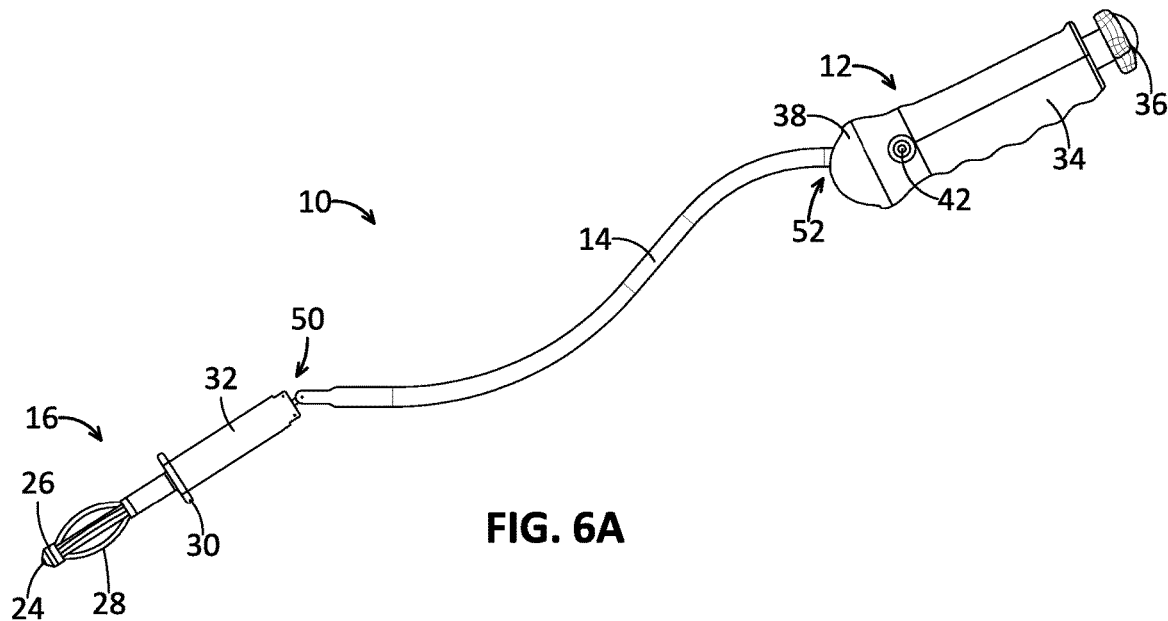
FIGS. 6A-6C are side views of the uterine manipulator of FIG. 1 in different pivoting positions.
Figure 6B:
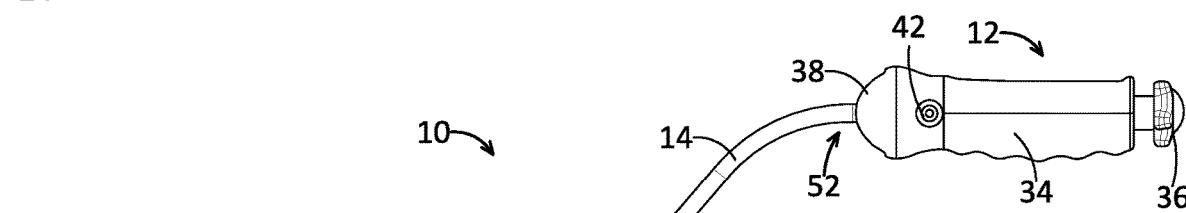
Figure 6C:
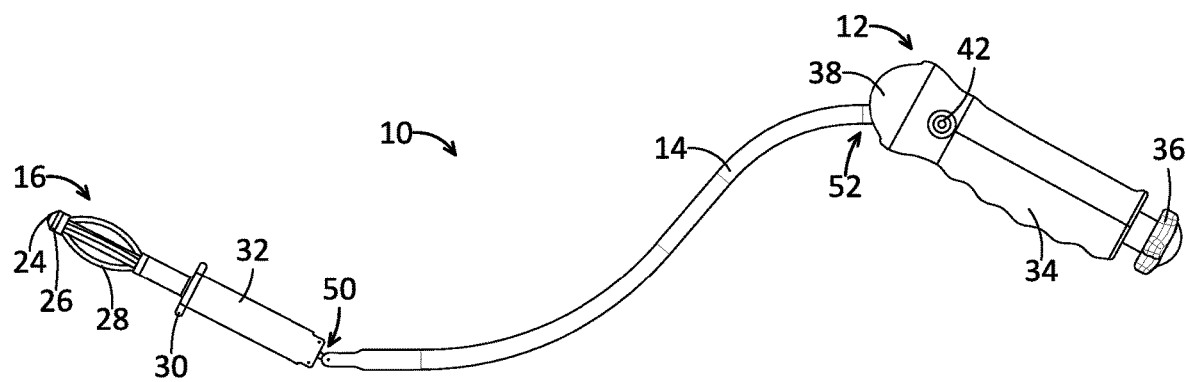
Figure 7A:
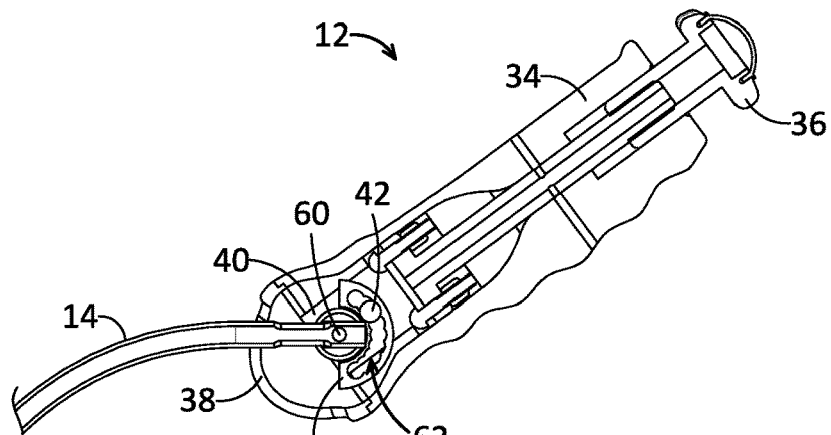
FIGS. 7A-7D are side and front views of the handle assembly of the uterine manipulator of FIG. 1 in different pivoting positions.
Figure 7B:
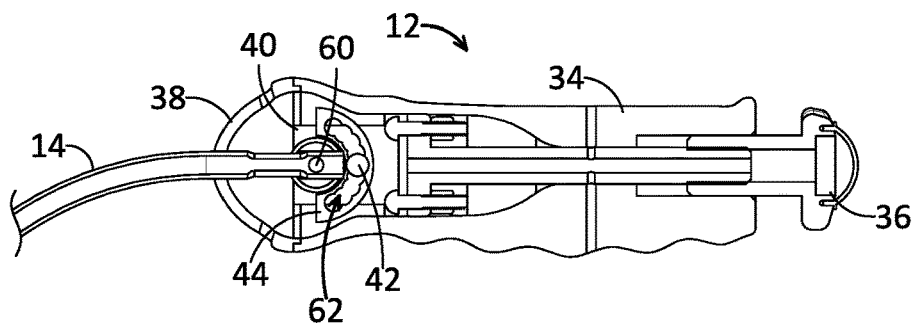
Figure 7C:
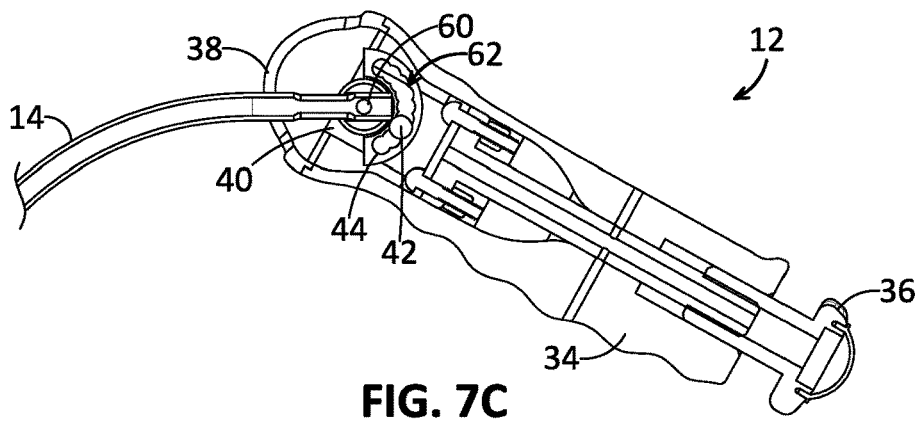
Figure 7D:
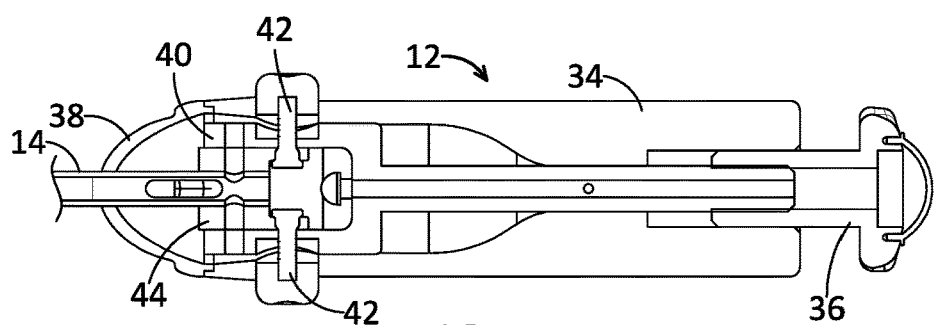

As shown in FIGS. 6A-6C, the tip assembly 16, the shaft 14, and the handle 12 can be pivotable relative to each other at two separate pivot points 50, 52. The first pivot point 50 and the second pivot point 52 can facilitate insertion of the uterine manipulator 10 into the uterus 114 and can also facilitate repositioning of the uterus 114 during a hysterectomy. The first pivot point 50 can be located at the connection between the tip housing 32 and the shaft 14. For example, as shown in FIGS. 4B and 5B, the end 54 of the tip housing 32 can be positioned between end components 56 of the shaft 14 so that through holes 58 in each component 54, 56 are aligned, and a pin 60 can be routed through the through holes 58 to permit a pivotable connection. The second pivot point 52 can be located at the connection between the shaft 14 and the handle 12. For example, as shown in FIGS. 4A, 5A, and 7A-7D, the shaft 14 can be fixed to the pivoting element 44 (e.g., via a pin 60 and through hole 58 connection) and the pivoting element 44 can be pivotable about the hinge 40 within the handle housing 34. The hinge pins 42 can extend through the handle housing 34, the hinge 40, and a track 62 of the pivoting element 44, as best shown in FIG. 7D. The track 62 can be ribbed so that the pivoting element 44 cannot freely slide within it. Rather, the pivoting element 44 can be substantially fixed at specific points along the ribbed track 62 and only adjusted by applying an amount of force. This can prevent unwanted movement of the second pivot point 52 unless a deliberate force is applied.

In at least one embodiment, an additional mechanism (for example, in the handle 12), can be used to control both pivot points 50, 52. For example, if the additional mechanism is actuated in a first direction, both pivot points 50, 52 can be locked in place. If the additional mechanism is actuated in a second direction, both pivot points 50, 52 can be unlocked and maneuverable. The shaft 14 can be constructed of a non-rigid, flexible material to facilitate insertion of the uterine manipulator 10 into the uterus 114.

Figure 8A:
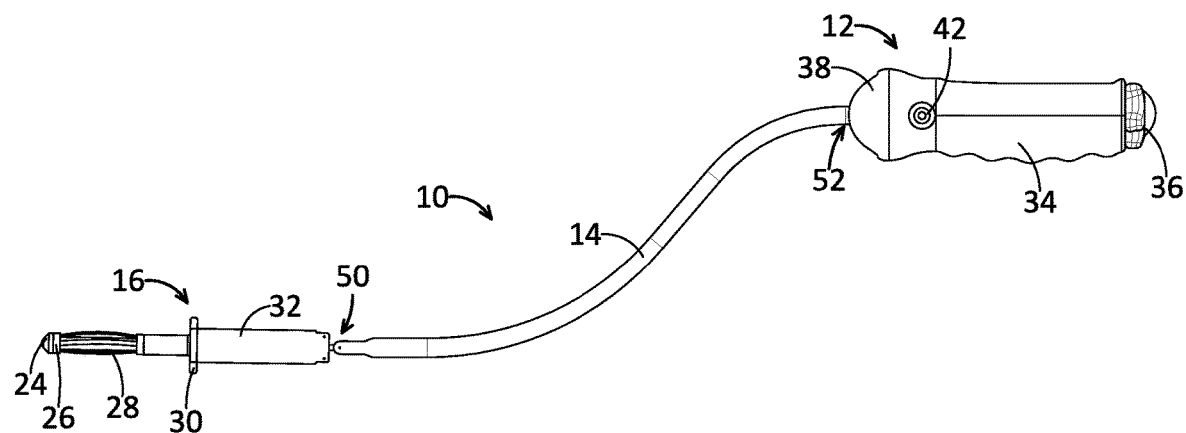
FIGS. 8A and 8B are side views of the uterine manipulator of FIG. 1 in a retracted position and an expanded position, respectively.
Figure 8B:
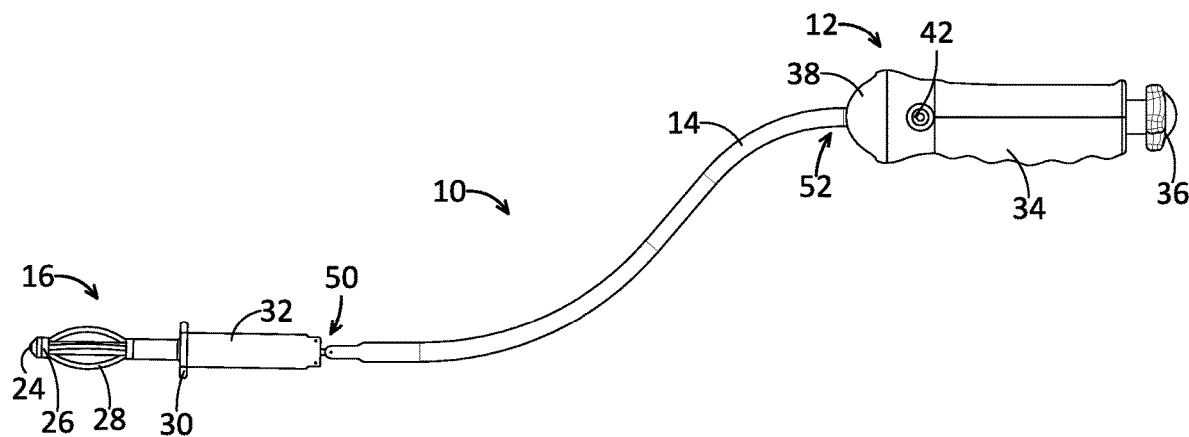
Figure 9A:
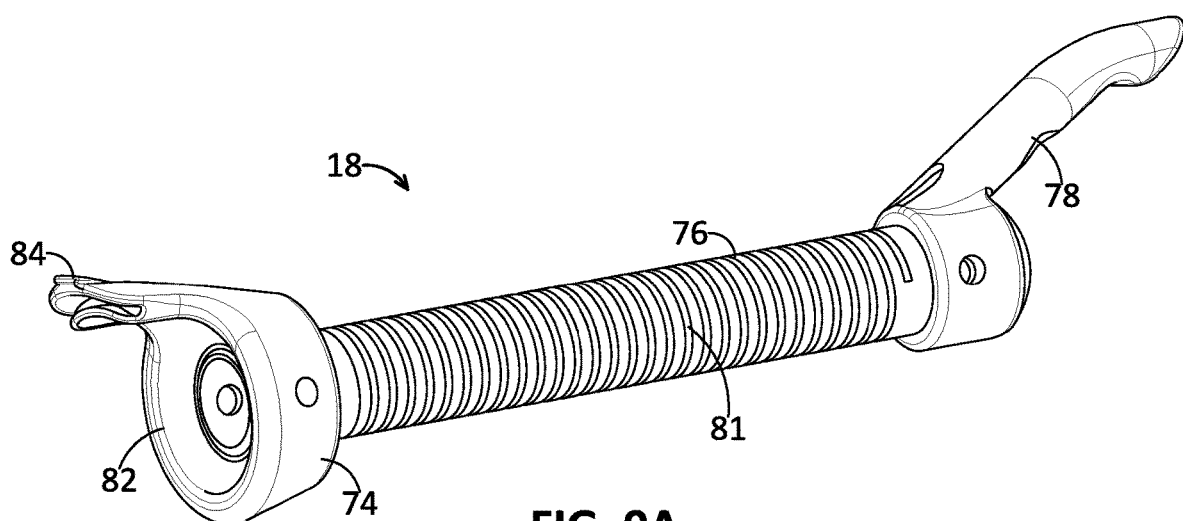
FIGS. 9A and 9B are perspective views of a cutting assembly and a backstop, respectively, of the uterine manipulator of FIG. 1.
Figure 9B:
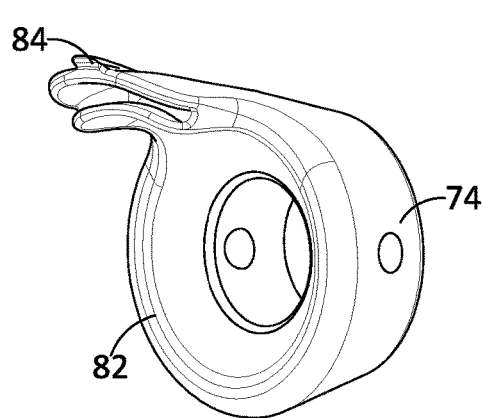

The tip assembly 16 can act as an umbrella-like expansion component capable of being adjusted between a retracted position and an expanded position. As a result, the tip assembly 16 can replace conventional intra-uterine balloon elements. The tip assembly 16 can be situated into the retracted position, as shown in FIGS. 8A and 12B, to facilitate insertion into the uterus 114 (e.g., until the abutment 30 reaches the cervix 112). Once inserted into the uterus 114, the tip assembly 16 can be deployed into the expanded position, as shown in FIGS. 8B and 12C, to facilitate a secure connection between the uterine manipulator 10 and the uterus 114 and cervix 112.

The expansion elements 28 can be spring-like elements capable of being in compression (e.g., shortened in length) and in tension (e.g., lengthened). Pulling the expansion actuator 36 away from the handle housing 34 can cause the expansion elements 28 to compress and expand outward circumferentially, situating the tip assembly 16 into the expanded position. Pushing the expansion actuator 36 back into the handle housing 34 causes the expansion elements 28 to retract back into tension and lengthen, situating the tip assembly 16 into the retracted position. Alternatively, the expansion actuator 36 can be twisted or rotated, rather than pulled and pushed from the handle housing 34, to adjust the expansion elements 28.

As shown in FIGS. 4B and 5B, the expansion tip 24 can slide into the tip shaft 26 until an end stop 64 of the expansion tip 24 reaches the end 66 of the tip shaft 26. The expansion elements 28 can fit over the tip shaft 26 until a first end 68 of the expansion elements 28 reaches the end 66 of the tip shaft 26. Both the expansion tip 24 and the tip shaft 26 can be slid into the tip housing 32, while the second end 70 of the expansion elements 28 can rest against an outer edge 72 of the tip housing 32. Pulling the expansion actuator 36 outward from the handle housing 34 causes the expansion connectors 48 to pull the expansion tip 24, and the tip shaft 26, further into the tip housing 32. Because the expansion elements 28 rest against the edge 72 of the tip housing 32, they are compressed (i.e., shortened in length) when the expansion tip 24 and the tip shaft 26 are forced into the tip housing 32. Shortening of the expansion elements 28 causes them to expand in their circumferential direction, therefore situating the tip assembly 16 into the expanded position. In the reverse, pressing the expansion actuator 36 back into the housing releases the pulling tension of the expansion connectors 48 on the expansion tip 24. The expansion elements 28 can be in a resting state when in tension and thus, without the pulling tension by the expansion connectors 48, the expansion elements 28 will revert back to their resting, retracted state, thereby pulling the expansion tip 24 and the tip shaft 26 back out from the tip housing 32 and situating the tip assembly 16 into the retracted position.

Figure 10A:
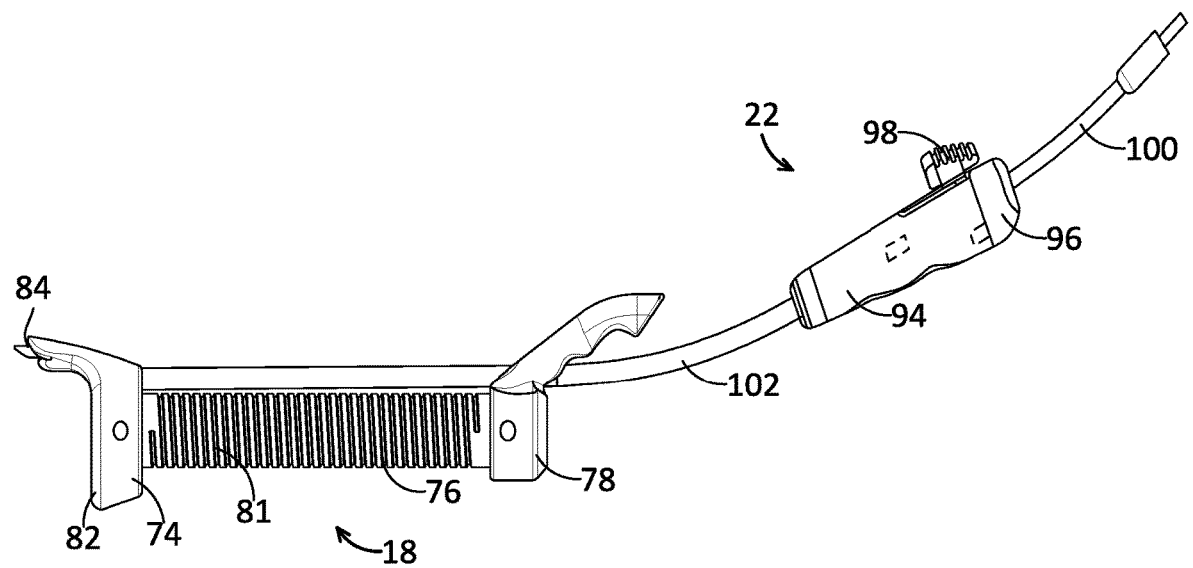
FIGS. 10A and 10B are side views of the cutting assembly and an electrical connector assembly, respectively, of the uterine manipulator of FIG. 1.
Figure 10B:
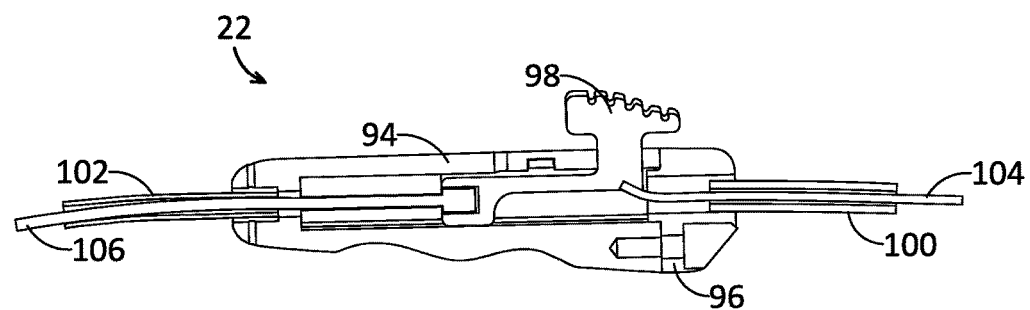
Figure 12D:
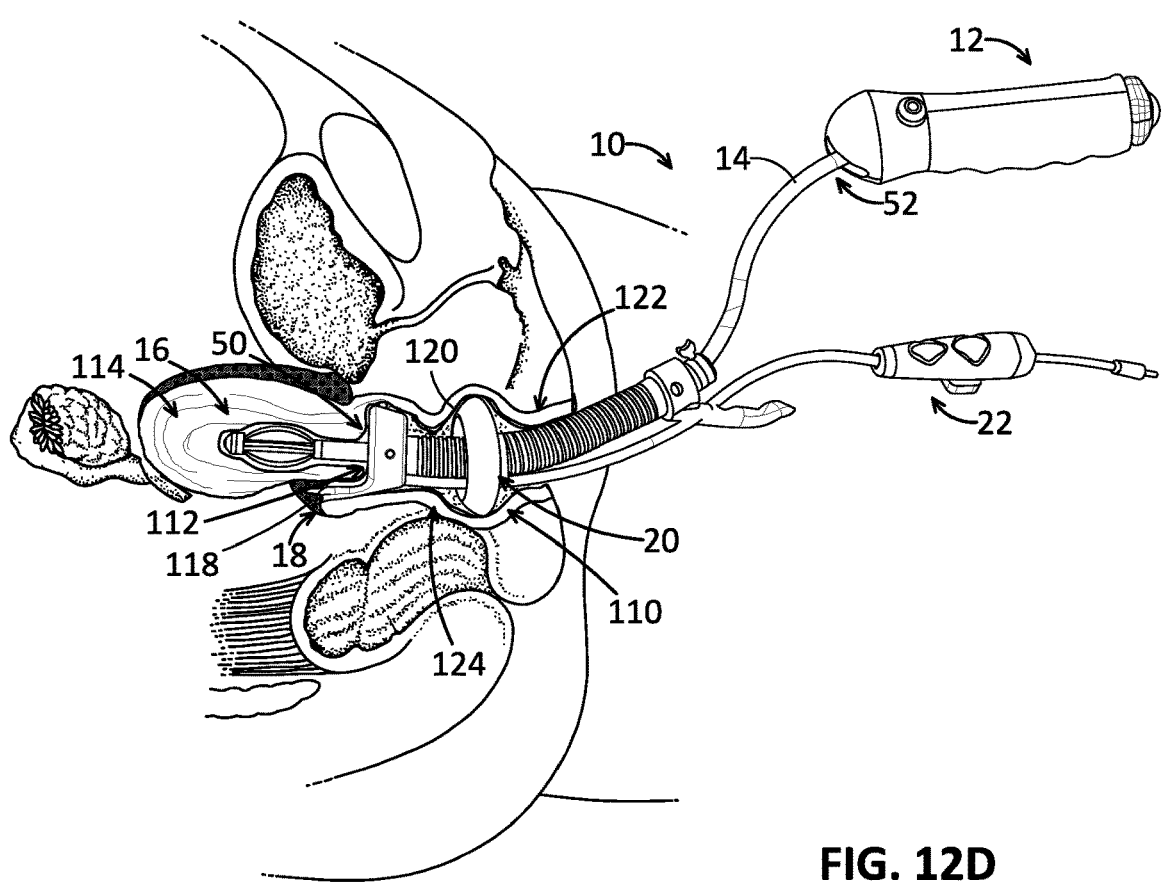

Referring back to FIGS. 1 and 2, the cutting assembly 18 can be slid over the shaft 14 and can be rotatable about the shaft 14. The cutting assembly 18 can include a backstop 74, a tube 76, a cutting handle 78, fasteners 80, and a spring 81. The backstop 74 can be positioned at a first end of the tube 76 and the cutting handle 78 can be positioned at a second, opposite end of the tube 76. The tube 76 can be slid over the shaft 14 and the cutting handle 78 can help maneuver the cutting assembly 18 along and/or around the shaft 14. The fasteners 80 can help fix the cutting assembly 18 in place along the shaft 14. The backstop 74 can receive the cervix 112 and come in contact with the vaginal fornix 118 when the uterine manipulator 10 is in position. The backstop can then be maneuvered in a circular manner to cut around the cervix 112 for detaching the cervix 112 and the uterus 114 from the vagina 110, as shown in FIG. 12D. As shown in FIGS. 10A and 10B, the backstop 74 can include a round cup portion 82 and a cutter 84 extending outward from the cup portion 82. During use, the cutting assembly 18 can be pressed up against the abutment 30 of the tip assembly 16 so that the cup portion 82 extends past the abutment 30 and engages the fornix, stretching and forcing the fornix upward and away from the ureters. The cutter 84 can pierce through the tissue of the fornix, transecting the uterus 114 and the cervix 112 from the top of the vagina 110.

The cutting assembly 18 can be rotated about the shaft 14 (e.g., by the cutting handle 78), allowing the cutter 84 to travel in a circle at the junction of the cervix 112 and the vagina 110 and permitting complete transection of the uterus 114 and the cervix 112 from the vagina 110. The spring 81 can help distribute rotational forces evenly across the tube 76 when the cutting assembly 18 is rotated, for example, to prevent the tube 76 from breaking due to excess torque concentrated along one portion of the tube 76.

The electrical connector assembly 22 can advance the cutter 84 outward from the cup portion 82 to achieve the detachment procedure described above, and can retract the cutter 84 inward to facilitate insertion of the uterine manipulator 10 into the uterus 114 without piercing the vaginal walls 120 prior to proper positioning of the uterine manipulator 10. The electrical connector assembly 22 can provide an electrical connection between the cutter 84 and an electrosurgical unit (not shown) in order to provide hemostasis during the detachment procedure. The electrical connector assembly 22 can include a handle 94, a cap 96, a button 98, tubing 100, 102, and electrical connectors 104, 106. On one end of the electrical connector assembly 22 (i.e., adjacent to the cap 96), the tubing 100 and the electrical connectors 104 can be routed to the electrosurgical unit. On the other end of the electrical connector assembly 22, the tubing 102 and the electrical connectors 106 can be routed to the cutter 84. The electrical connectors 104, 106 can be electrically connected through the button 98 so that current can be routed from the electrosurgical unit to the cutter 84. The electrical connectors 106 can be coupled to the cutter 84 and the button 98 so that pressing the button 98 forward and backward causes the cutter 84 to extend and retract, respectively.

Figure 11:
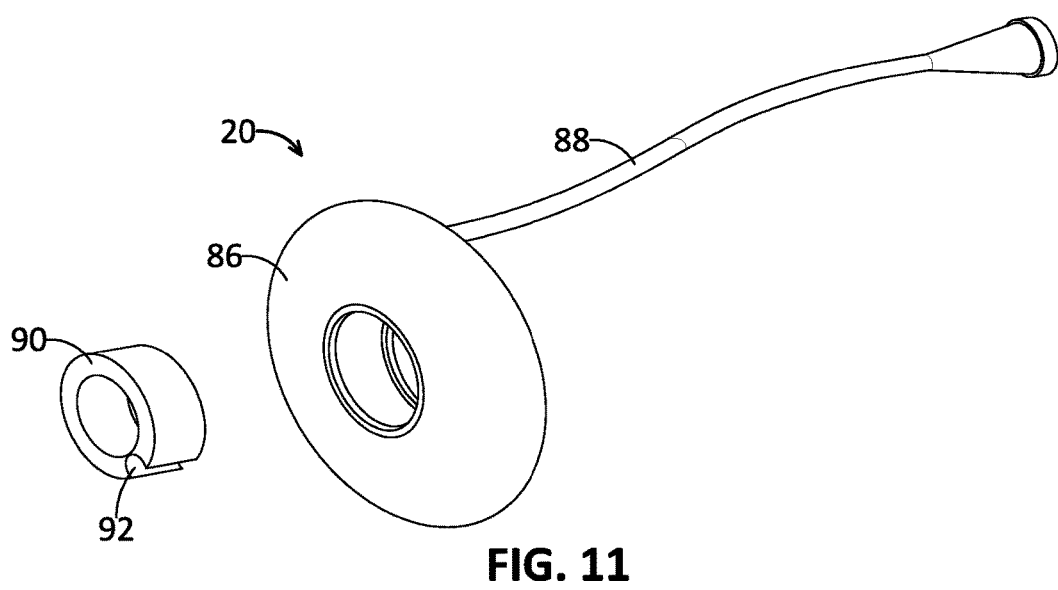
FIG. 11 is a perspective view of a pneumooccluder of the uterine manipulator of FIG. 1.

Referring to FIG. 11, the pneumooccluder 20 can include a balloon 86, a filling tube 88, and a bearing 90. The bearing 90 can be in contact with the tube 76 of the cutting assembly 18, and the balloon 86 can be positioned around the bearing 90. As shown in FIG. 11, the bearing 90 can include an outer groove 92 to allow passage of the electrical connector assembly tubing. During use, the pneumooccluder 20 can be positioned within the vagina 110 when the uterine manipulator 10 is set within the uterus 114. Once in position, the balloon 86 can be inflated via the filling tube 88 (e.g., with air, water, saline, or another fluid) in order to seal the distal vaginal cavity 122 from the proximal vaginal cavity 124. This can help maintain pneumoperitoneum once the incision has been made between the vagina 110 and the cervix 112 (i.e., causing the proximal vaginal cavity 124 to be in fluid communication with the abdominal cavity). As a result of the bearing 90, the shaft 14 and/or the cutting assembly tube 76 can be rotated without requiring rotation of the balloon 86. Because the balloon 86 can be set in place and does not need to be rotated when the shaft 14 or the cutting assembly 18 is rotated, the risk of losing pneumoperitoneum is greatly reduced.

Thus, the uterine manipulator 10 can be inserted into a patient's vagina 110 while in the retracted position, as shown in FIG. 12A. The uterine manipulator 10 can then be further guided through the vagina 110, past the cervix 112, and into the uterus 114, while still in the retracted position, as shown in FIG. 12B. Once set in the uterus 114, the uterine manipulator 10 can be situated into the expanded position, as shown in FIG. 12C, in order to facilitate a secure connection between the uterine manipulator 10 and the uterus 114. Once the uterine manipulator 10 is set within the uterus 114, the pneumooccluder 20 can contact the vaginal wall 120 in order to seal the uterus 114 from the outside environment and the backstop 74 can abut the vaginal fornix 118, causing it to stretch upward. Once the uterine manipulator 10 is situated into the expanded position, the cutter 84 can be extended and the cutting handle 78 can be rotated in order to transect the uterus 114 and the cervix 112 from the top of the vagina 110. The uterine manipulator 10 of the present invention and its above-described procedures can thus eliminate the need for a colpotomy incision via laparoscopic tools, as in conventional laparoscopic and robotic hysterectomies.

At least one embodiment can include any combination of one or more of the above-described components and/or other conventional uterine manipulator components. The above-described components, such as the cutting assembly 18, the tip assembly 16, and the pneumooccluder 20 can function independently from one another and therefore can be individually incorporated into a uterine manipulator with or without the other components. For example, it may be preferable to include the pneumooccluder 20 as described above with some previous approaches to best execute a specific pelvic procedure.

Figure 13:
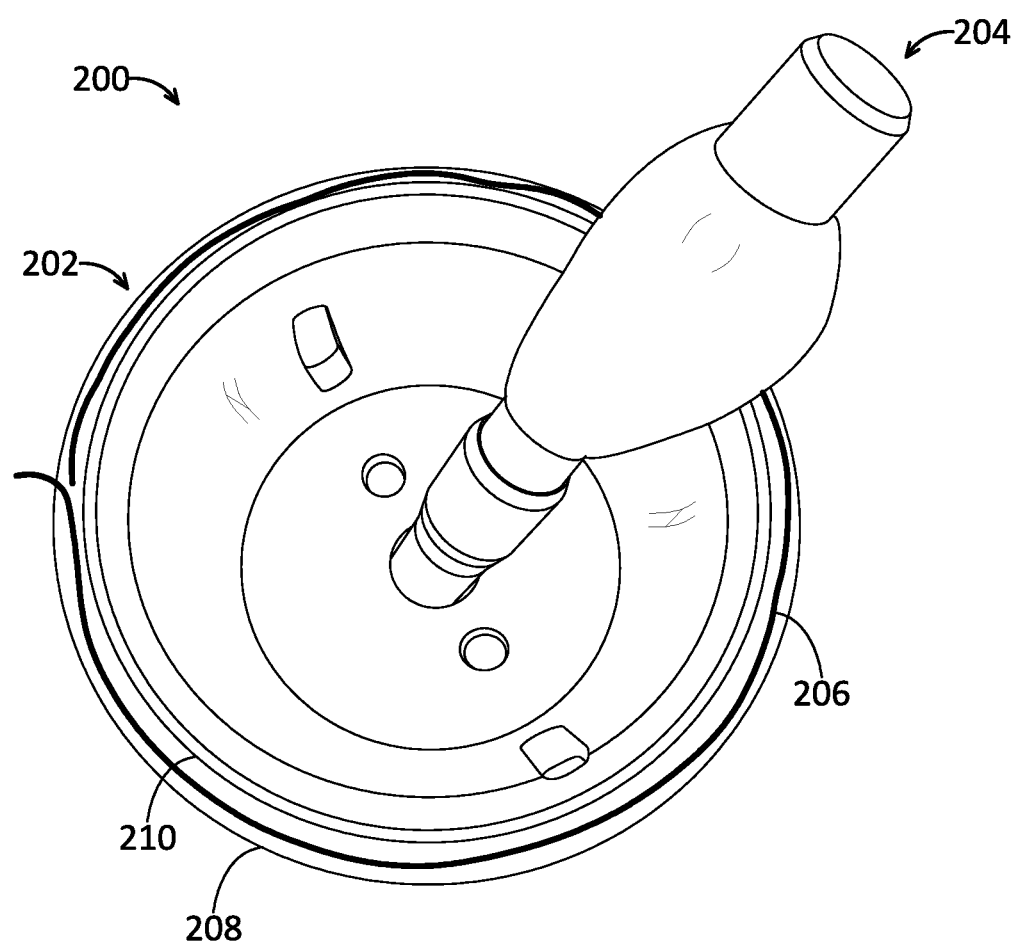
FIG. 13 is a perspective view of a manipulator, cup, and cutting assembly in accordance with the present disclosure.

Referring to FIG. 13, a cutting assembly 200 is illustrated. The cutting assembly 200 can be used with the functional uterine manipulator 10 of the preceding figures or can be used with other systems. The cutting assembly 200 includes a cup portion 202 and an expansion tip 204 extending therethrough. As illustrated in FIG. 13, the expansion tip 204 can be a balloon-type design or other configurations, such as described above. Associated with the cup portion 202 is a cutter or cutter wire 206. The cup portion 202 is designed to engage the cervix 112, such as previously described. The cutter 206 is formed as a narrow wire, with a looped tip, embedded between two grooves 208, 210 on the cup portion 202 (that is, around the circumference of the cup portion 202).

Figure 15A:
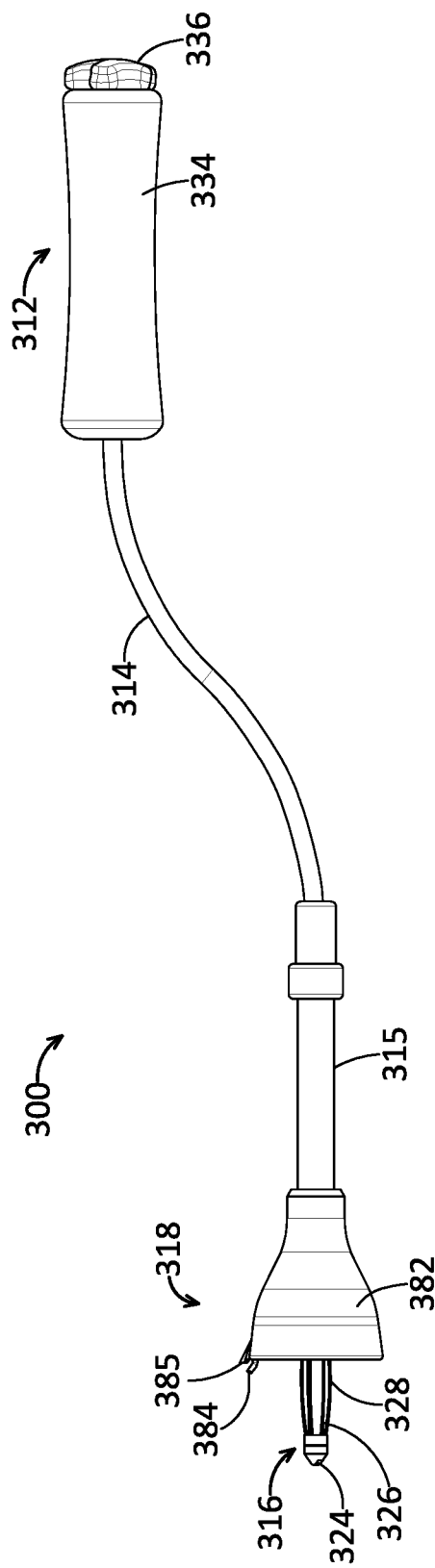
FIGS. 15A-15B are side views of a uterine manipulator in accordance with the present disclosure.
Figure 15B:
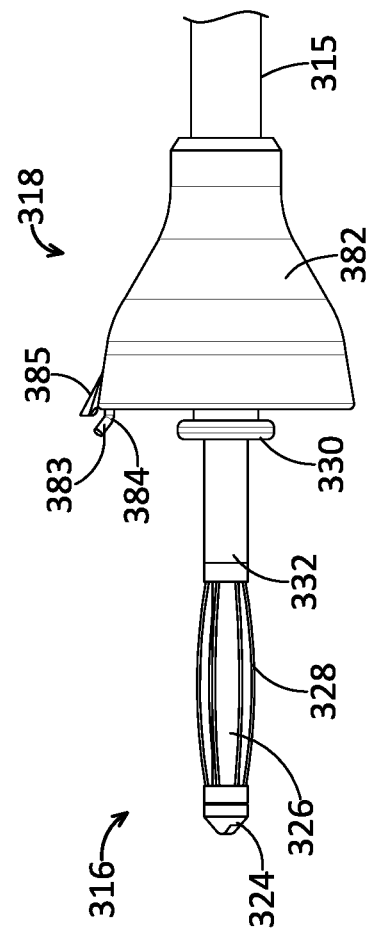

FIGS. 15A-15B illustrate another uterine manipulator 300. The uterine manipulator 300 can include a handle 312, a shaft 314, a tip assembly 316, and a cutting assembly 318. Unless otherwise stated, the elements of the uterine manipulator 300 can be similar in function and structure to those of the above-described uterine manipulator 100 of the previous figures. The uterine manipulator 300 can incorporate any of the above-described elements of the previous figures. For example, the tip assembly 316 can include an expansion tip 324, a tip shaft 326, umbrella-like expansion elements 328, an abutment 330, and a tip housing 332. The handle 312 can include a handle housing 334 and an expansion actuator 336. Twisting or rotating the expansion actuator 336 in a first direction causes the expansion elements 328 to compress and expand outward circumferentially, situating the tip assembly 316 into the expanded position. Twisting or rotating the expansion actuator 336 in a second, opposite direction causes the expansion elements 328 to retract back into tension and lengthen, situating the tip assembly 316 into the retracted position.

The cutting assembly 318 can be rotatable about the shaft 314. More specifically, as shown in FIGS. 15A-15B, the uterine manipulator 300 can include a flexible shaft portion 315 along which the cutting assembly 318 can slide laterally and/or rotated for proper positioning or operation. The cutting assembly 318 can include a cup portion 382 and a cutter or cutter wire 384. Similar to the cutter 206 of FIG. 13, the cutter 384 can be formed as a narrow wire, with a looped tip 383, embedded between grooves (not shown) on the cup portion 382. In addition, the cup portion 382 can include a projection 385 to assist an operator in locating the cutter 384 during an operation, to help shield the cutter 384 during insertion of the uterine manipulator 300, and/or to help push the cutter 384 through the vaginal tissue.

Figure 14:
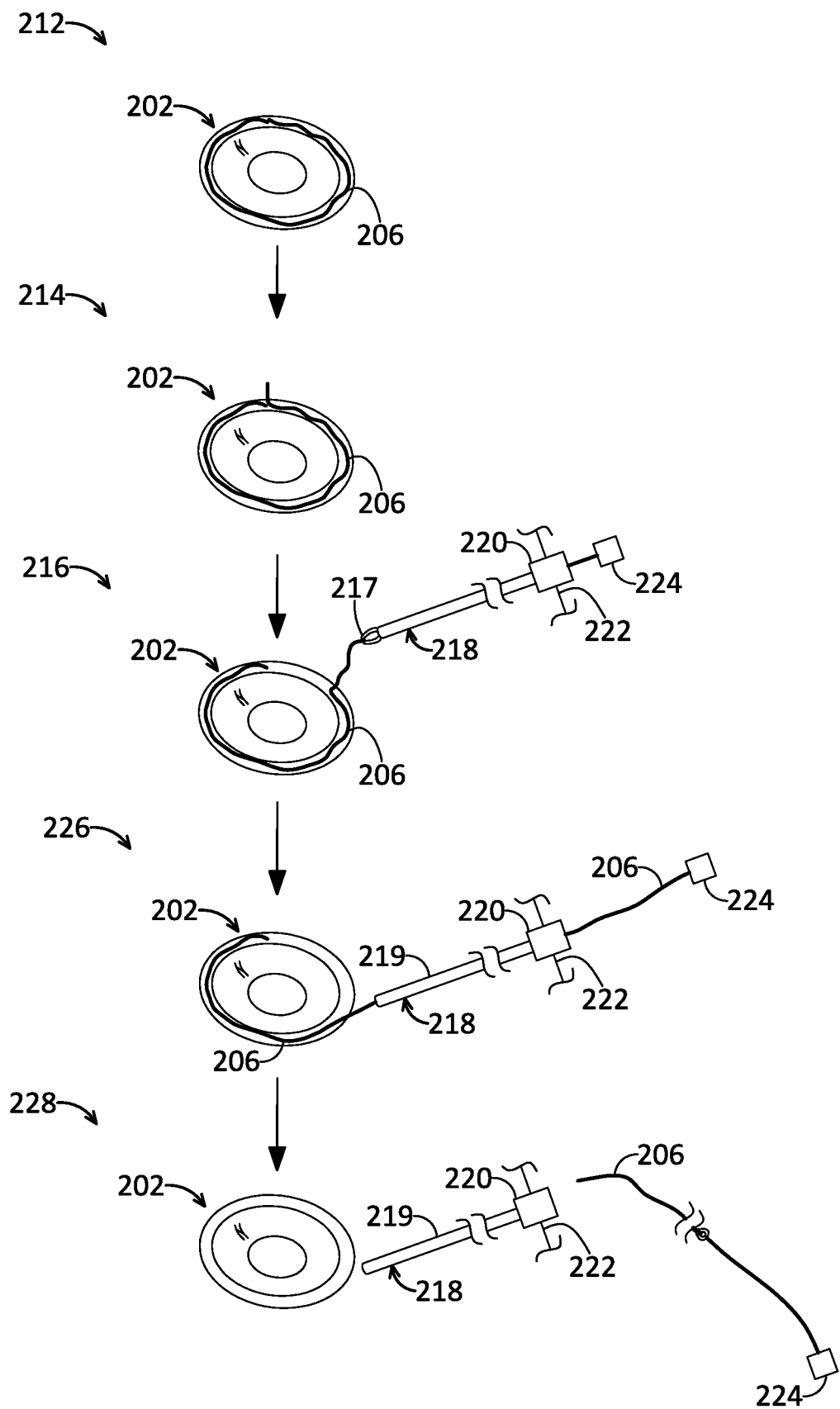
FIG. 14 is a series of views showing use of the cutting assembly of FIG. 13 in accordance with the present disclosure.

Referring to FIG. 14, the cutter 206 (or the cutter 384) is preset in a stored position 212 between the grooves 208, 210 (for example, when the uterine manipulator 100/300 is being inserted into a patient's uterus 114). The cutter wire can be secured between the grooves 208, 210 by small, thin bridges (not shown) around the edge of the cup portion 202, with the looped tip of the cutter 206 extending outward from the grooves 208, 210 at a 12 o'clock position. The bridges can be thin enough that they can be easily broken by pulling the cutter 206 against the bridges with sufficient force. The cutter 206 is designed to move from the stored position 212 to an extended position 214 where the cutter 206 can be pushed through the top of the vagina (for example, with the help of the projection 385 of cup portion 382 shown in FIGS. 15A and 15B) after the cup portion 202 has been positioned at a juncture between the cervix 112 and the vagina 110 (for example, the vaginal fornix 118). In a further extended position 216, the cutter 206 can be pulled in by a laparoscopic instrument 218, or "wand," that is introduced laparoscopically.

The instrument 218 includes a trocar 220 that extends through the skin 222 to present a handle 224 to a clinician. The instrument 218 also includes a small grasper 217 at its proximal end that can grasp or engage with the looped tip of the cutter 206. Using the handle 224, the instrument 218 is directed around the cup portion 202 and, as a result, pulls the cutter 206 at position 226. As the cutter 206 makes contact with tissue at the juncture of the vagina 110 and cervix 112, the tissue is cut, thus separating the vagina 110 from the cervix 112 and uterus 114. At a final position 228, for example, once the cutter 206 has been pulled around the circumference of the cup portion 202, the cutter 206 can be separated from the cup portion 202. The laparoscopic instrument, with the entire cutter 206, can then be removed through a laparoscopic port at the skin 222.

The inner groove 210 of the cup portion 202 can be taller than the outer groove 208 to prevent the cutter 206 from being pulled inward (instead of upward or outward) as the instrument 218 pulls the cutter 206. In addition, the laparoscopic instrument 218 can include an outer insulation cover 219 that is pushed forward while the cutter 206 is pulled out of the grooves 208, 210. That is, the cutter 206 is pulled into or received in the laparoscopic instrument 218 so that the cutter 206 is covered by the laparoscopic instrument 218 during operation, thereby enhancing safety given that the cutting wire or blade (which can be carrying electrical current, as described below) is not exposed at any given time.

The cutter 206 can either cut the vagina without electrical current ("cold") or with an electrical current, based on surgeon preference. For example, a distal end of the laparoscopic instrument 218 can connect to an electrosurgical unit (not shown) or electrical connector assembly, which can conduct monopolar or bipolar current. Accordingly, once the laparoscopic instrument 218 grasps the cutter 206, current is passed through the instrument 218 and to the cutter wire 206. Different operations can be conducted based on monopolar or bipolar configurations. For example, in a monopolar configuration, the cutter 206 can be pulled out of the cup portion 202 along its entire circumference and removed via the laparoscopic instrument 218 (as described above with reference to FIG. 14) while the cup portion 202 remains fixed to a shaft (such as shaft 14 or 314). More specifically, the cup portion 202 is not rotated about the shaft during this operation. Power during monopolar operation can be relatively high, such as about 100 watts.

Figure 16:
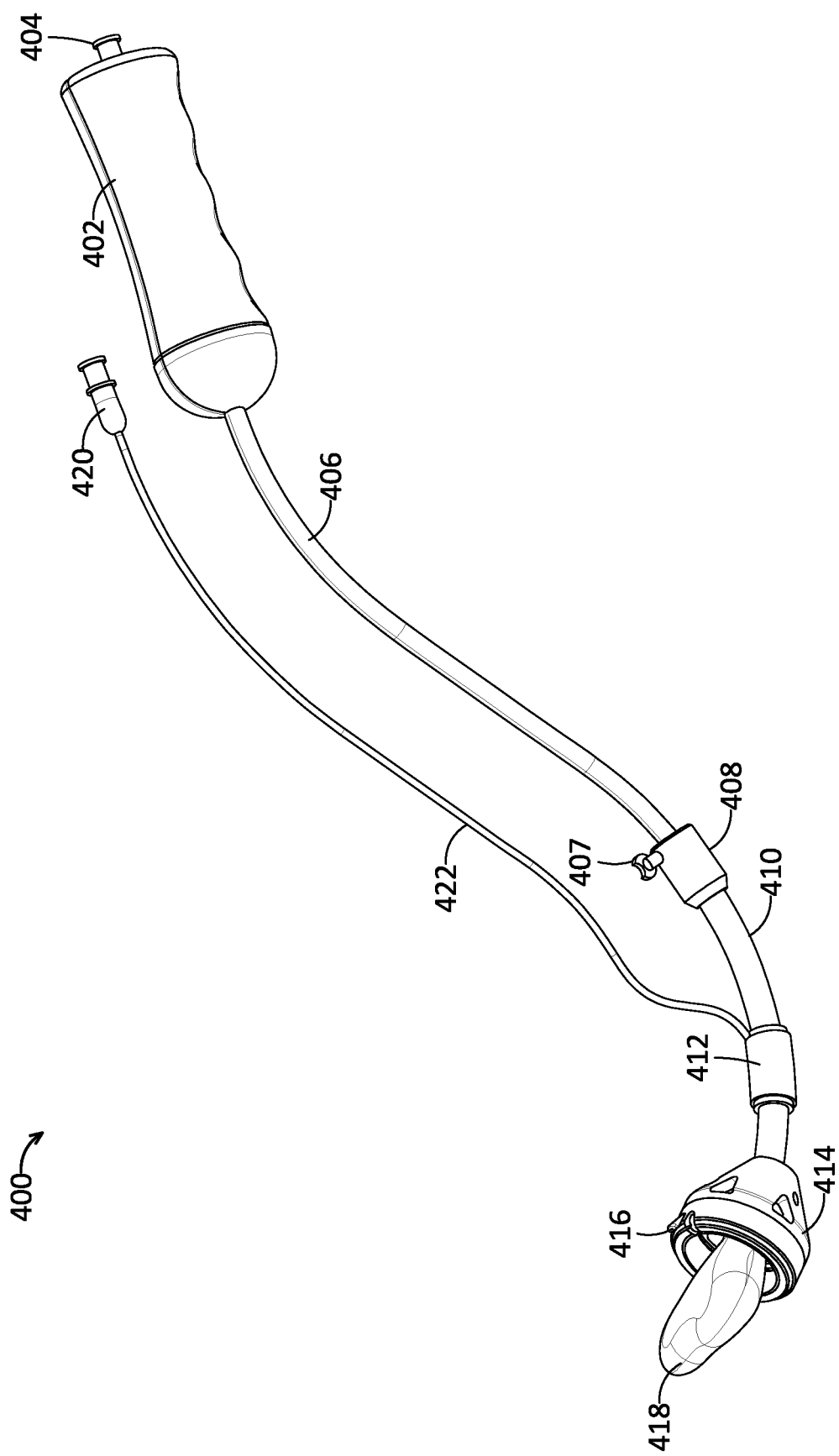
FIG. 16 illustrates a uterine manipulator in accordance with the present disclosure.

FIG. 16 illustrates a uterine manipulator 400 in accordance with the present disclosure. The uterine manipulator 400 can include a handle assembly 402 coupled to a distal end of a shaft 406. The handle assembly 402 is discussed further in association with FIG. 18 below. The handle assembly 402 and the shaft 406 can be analogous to the handle 12 and the shaft 14 illustrated in FIGS. 1-2, respectively. The shaft 406 can be substantially S-shaped. The uterine manipulator 400 can include a sheath 410, which can slide over and along the exterior surface of the shaft 406. The sheath can be heat shrunk around the shaft 406. The uterine manipulator 400 can include a stopper 408 that slides over and along the exterior surface of the shaft 406 and interfaces with the proximal end of the sheath 410. The stopper 408 includes a key 407 that can engage with the shaft 406. Engaging the key 407 with the shaft 406 can prevent the stopper 408 and the sheath 410 from sliding distally along the exterior surface of the shaft 406. The stopper 408 and the key 407 are discussed further in association with FIGS. 17A-17B below.

The uterine manipulator 400 can include a pneumooccluder 412, which can slide over and along the exterior surface of the sheath 410. A filling tube 422 can be coupled to the pneumooccluder 412 and can include fluid inlet 420 for the pneumooccluder 412. The pneumooccluder 412 and the filling tube 422 can be analogous to the pneumooccluder 20 and the filling tube 88 illustrated in FIGS. 1-2, respectively. A cup 414 coupled to the sheath 410 at or near the distal end of the sheath 410. The cup 414 can be configured to be positioned at a juncture between a patient's cervix and vagina. The cup 414 can include a cap 416. The cap 416 can be coupled to the cup 414 at a distal end of the cup 414. The cup 414 is discussed further in association with FIGS. 19A-20 below. At least one embodiment does not include the cup 414 and the cap 416.

Figure 17:
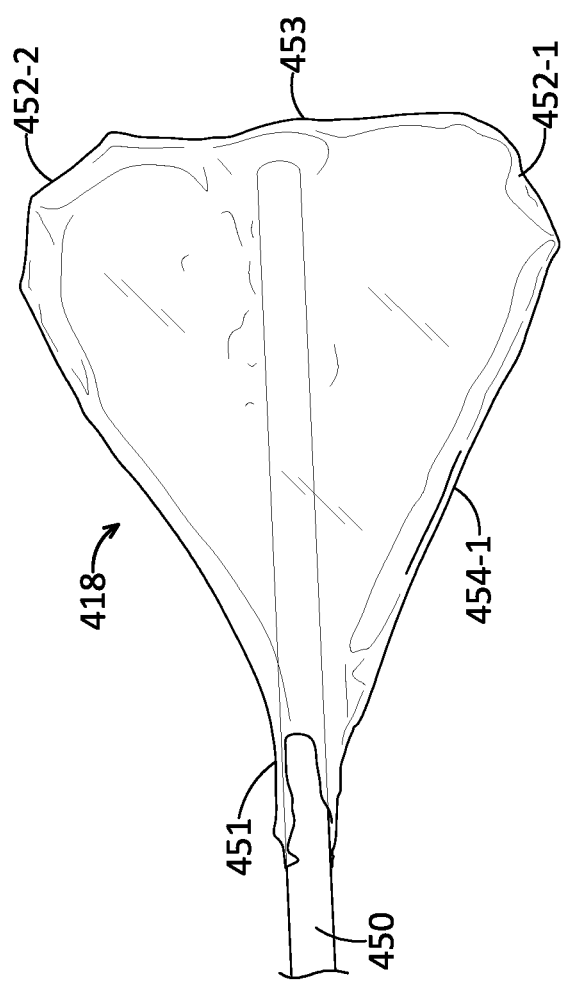
FIG. 17 illustrates the distal portion of the uterine manipulator and the balloon in accordance with the present disclosure.

FIG. 17 illustrates the distal portion of a uterine manipulator and the balloon 418 in accordance with the present disclosure. The balloon 418 can be triangular in shape. The triangular shape can mimic the interior contours of a patient's uterus. The triangular shape can be similar to that of an isosceles triangle, for example. The corners 452-1 and 452-2 of the balloon 418, where the base 453 meets each of the legs 454-1 and 454-2, can be rounded or cut off to better mimic the interior contours of a patient's uterus. The balloon 418 can be coupled to a tube 450 at the point 451 where the legs 454-1 and 454-2 of the balloon 418 meet. As shown in FIG. 17 the tube can protrude into the volume of the balloon 418 such that that the distal end of the tube 450 almost contacts the base 453 of the balloon 418. The tube 450 can include steel. The tube 450 can be coupled to the shaft 406 or comprise the shaft 406. The balloon can include a thermoplastic polyurethane (TPU) material.

Figure 18:
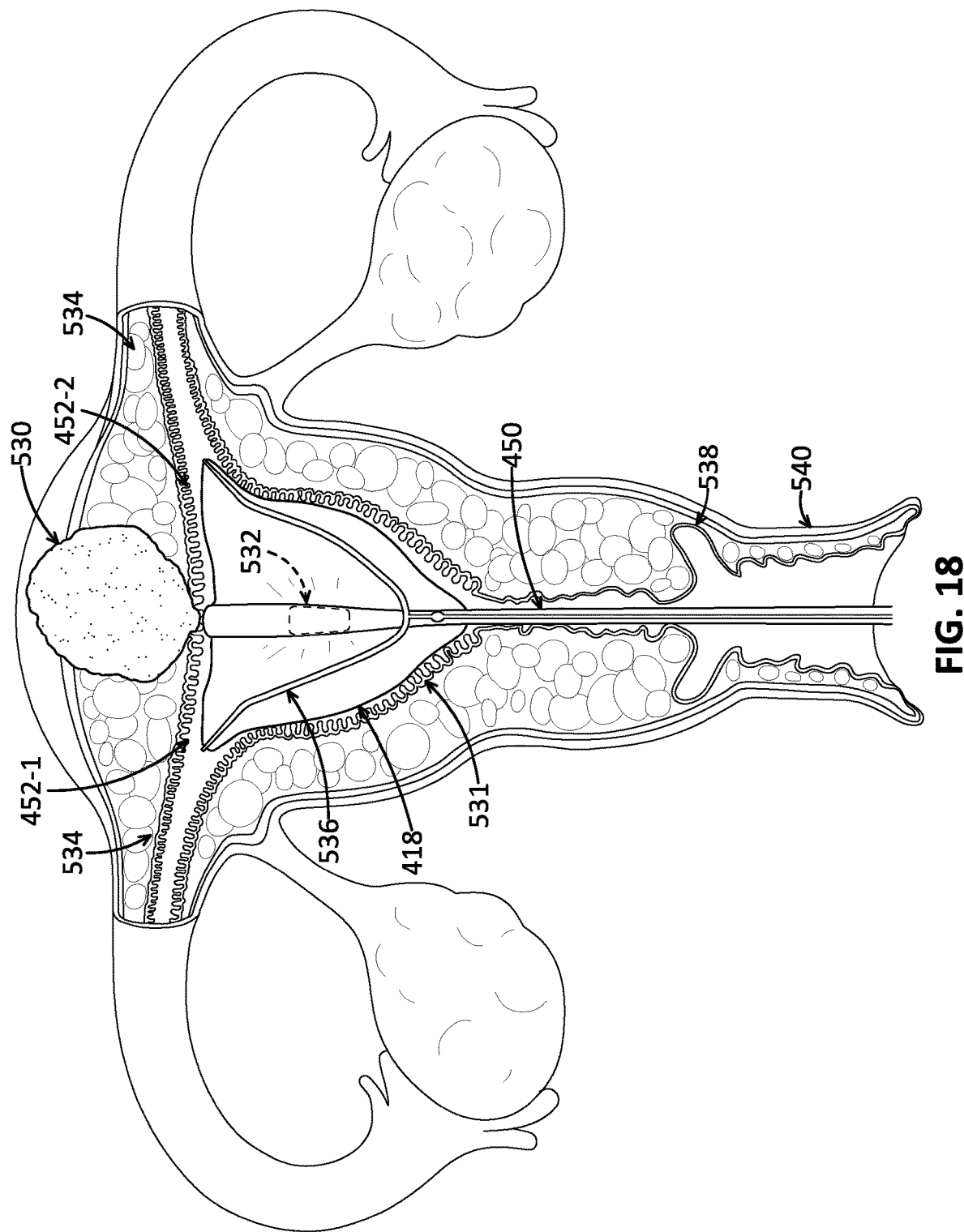
FIG. 18 illustrates the distal portion of a uterine manipulator and the balloon 418 in accordance with the present disclosure inserted into a patient's uterus.

FIG. 18 illustrates the distal portion of a uterine manipulator and the balloon 418 in accordance with the present disclosure inserted into a patient's uterus 531. The distal portion of the uterine manipulator, such as the uterine manipulator 400 illustrated in FIG. 16, can be inserted into a patient's uterus 531 via the patient's vagina 540 and cervix 538. As illustrated in FIG. 18, the corners 452-1 and 452-2 of the balloon 418 can include apertures and/or channels 536. For example, dye can be injected into the balloon 418 via the channels 536, such as that used in chromopertubation in order to determine the patency of one or both fallopian tubes. Because the balloon 418 mimics the interior contours of a patient's uterus 531, the corners 452-1 and 452-2 can be aligned with the openings of the fallopian tubes 534 with little or no adjustment of position and/or orientation of the inflated balloon 418 in the patient's uterus 531. Thus, when dye is injected into the balloon 418 the dye flows directly from the corners 452-1 and 452-2 into the openings of the fallopian tubes 534 so as to avoid inadvertent injection of dye into muscular tissue of the uterus.

As illustrated in FIG. 18, the balloon 418 can include a light source 532, such as a light emitting diode (LED) or fiber optics. The light source 532, for example, can be coupled to the tube 450. The light source 532 can illuminate the interior of a patient's uterus 531. The light output of the LED (or LEDs) can range from about 100 lumen to about 10,000 lumen, in increments of about one lumen. An array of LED elements can be provided coupled to a controller that can controllably adjust the temperature (e.g., 2700 K to 5000 K in increments of 10K) and/or color of the LEDs to produce, for example, shades of white light of varying warmth by relatively increasing the amount of yellow or blue output of the LEDs. Thus, an LED array having LEDs of different colors (yellowish white to bluish white) can be provided. For example, the array can have three (red, green blue LEDs), four, five, six, seven, eight, nine, ten, eleven or twelve different colors of LEDs to permit color mixing. For example, the controller can create a light output having a peak light output between about 365 nm and about 700 nm in increments of about 5 nm.

Using visualization from inside a patient's uterus 531 (e.g., using a separate endoscope, using an endoscope disposed along a separate sleeve formed into the shaft, or by using an optic integrated into the balloon, such as a photodetector array, not show), in addition to or as a component of the uterine manipulator, the endometrial lining of the patient's uterus 531 can be examined, for example, for perforations during a myomectomy. Avoiding undetected perforations in the endometrium can increase patient safety and/or the fertility of the patient. If the light source has a high intensity, a patient's uterus can be illuminated internally but visualized externally to, for example, identify and/or locate fibroids, such as the fibroid 530. Such external visualization can be accomplished, for example, but introducing an endoscope into an insufflated abdominal cavity. The camera of the endoscope can thus view light originating from within the uterus and shining through the tissue of the uterus.

Figure 19B:
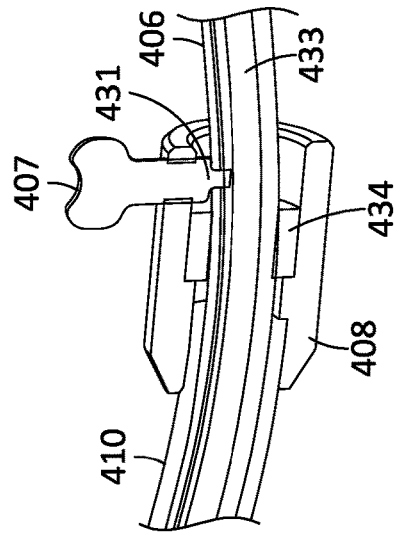
FIG. 19B illustrates a cross-sectional view of the stopper and the key of FIG. 16.
Figure 19A:
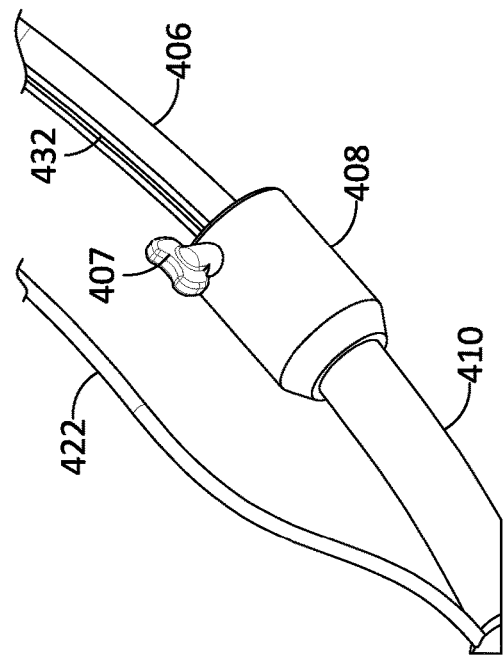
FIG. 19A illustrates a partial perspective view of the uterine manipulator of FIG. 16.

FIG. 19A illustrates a partial perspective view of the uterine manipulator 400 of FIG. 16. As shown in FIG. 19A, the shaft 406 can include a groove 432. The groove 432 can run along a portion of the shaft 406 beginning at the proximal end of the shaft or the full length of the shaft 416. The groove 432 can be used to orientate rotationally at least one component of the uterine manipulator 400, such as the handle assembly 402 or the cup 414. The key 407 can engage with the shaft 406 via a protrusion 431 of the key 407 that fits in the grove 432. The stopper 408 can have a sloped distal end.

FIG. 19B illustrates a cross-sectional view of the stopper 408 and the key 407 of FIG. 16. As shown in FIG. 19B the shaft 416 interfaces the stopper 408 via a gasket 434. The gasket 434 can prevent liquid/gas leaks from the sheath 410. The proximal end of the sheath 410 interfaces with the distal end of the stopper 408. As shown in FIG. 19B, the shaft 416 can include a channel 433. The channel of the shaft 406 can, for example, transport fluid to inflate the inflatable balloon 418. The key 407 can include a protrusion 435 that engages the shaft 406 via the groove 432.

Figure 20:
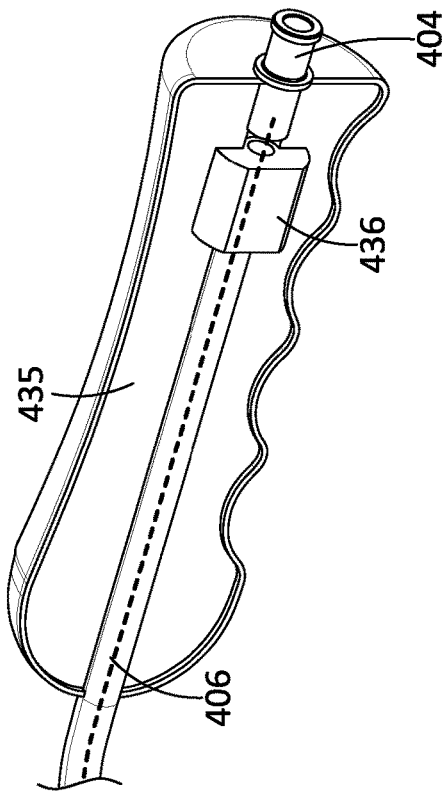
FIG. 20 illustrates a cross-sectional view of the handle assembly of FIG. 16.

FIG. 20 illustrates a cross-sectional view of the handle assembly 402 of FIG. 16. The handle assembly 402 can include a fluid inlet 404, which can be located at the proximal end of the handle assembly 402. The handle assembly 402 can include a proximal portion of the shaft 402 illustrated in FIG. 16. As shown in FIG. 20, the proximal end of the shaft 406 can be coupled to a locking block 436. An inlet tube (not shown) can be coupled to the locking block 436 and the fluid inlet 404. The locking block 436 can include a channel to allow fluid and/or other equipment (e.g., a stylet) to pass through the fluid inlet 404, the inlet tube, and the locking block 436 and into the shaft 406. The handle 435 can surround at least a portion of the fluid inlet 404, the inlet tube, the locking block 436, and the shaft 406. Although not shown in FIG. 20, the handle assembly 402 can include apertures and/or channels for wires 450-1 and 450-2 illustrated in FIG. 22.

Although not illustrated in FIG. 20, the handle assembly 402 can include a trigger. The trigger can be coupled to a needle in the cup 414 as described in association with FIG. 16 above. The needle in the cup 414 can be used to introduce the wire.

Figure 21B:
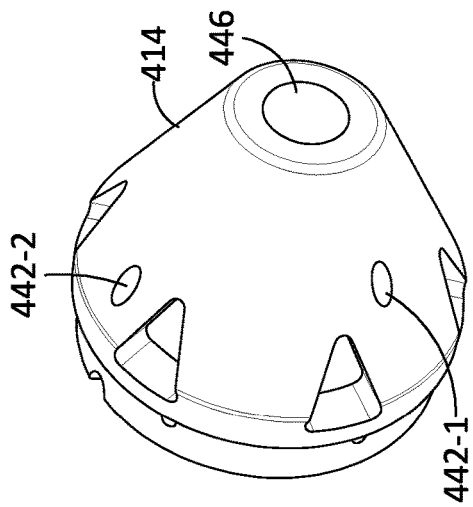
FIG. 21B illustrates another perspective view of the cup of FIG. 16.
Figure 21C:
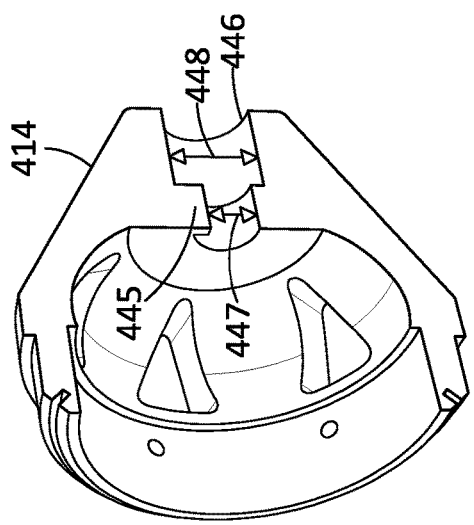
FIG. 21C illustrates a cross-sectional view of the cup of FIG. 16.
Figure 21A:
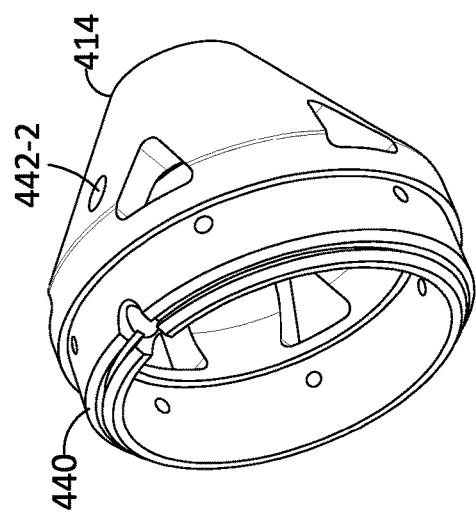
FIG. 21A illustrates a perspective view of the cup of FIG. 16.

FIG. 21A illustrates a perspective view of the cup 414 of FIG. 16. The cup 414 can have a conical shape. The distal end of the cup 414 includes an interface 440 for the cap 416 illustrated in FIG. 16. The cup 414 is configured to interface with a patient's cervix.

FIG. 21B illustrates another perspective view of the cup 414 of FIG. 16. The cup 414 can include aperture 446 through which the shaft 416 can pass through. As shown in FIG. 21B the cup 414 can include apertures 442-1 and 442-2 for passing wires through for powering a cutting head (discussed further in association with FIG. 22 below) or for any other desired purpose.

FIG. 21C illustrates a cross-sectional view of the cup 414 of FIG. 16. As shown in FIG. 21C, the aperture 446 can include a first diameter 447 for the shaft 406 and a larger second diameter 448 (e.g., a counter bore) for a sheath 410 illustrated in FIGS. 16 AND 22. The aperture 446 can include a projection 445 that can fit into the groove 432 illustrated in FIG. 19A to maintain proper orientation of the cup 414 relative to the shaft 406.

FIG. 22 illustrates a distal portion of the uterine manipulator 400 of FIG. 16. The pneumooccluder 412 the cup 414 are shown as see-through. However, embodiments are not limited to the pneumooccluder 412 and/or the cup 414 including a transparent material. In at least one embodiment, the uterine manipulator 400 can include a heat shrink sleeve 452 that surrounds the sheath 410 from the stopper 408 to the cup 414. As shown in FIG. 22 wires 450-1 and 450-2 pass through apertures in the stopper 408, run adjacent to the heat shrink sleeve 452, pass under the pneumooccluder 420, and pass through the apertures 442-1 and 442-2, respectively. It will be appreciated that conductors/wires can be routed in other manners.

In a bipolar configuration, the cutter 206 can be a shorter wire than the monopolar configuration, for example, about 2 centimeters (cm) to about 3 cm. The cutter 206 can be pulled through the vaginal tissue by the laparoscopic instrument 218, remaining at the 12 o'clock position, and then the cup portion 202 can be rotated about the shaft as the cutter 206 is held in place. One pole of the bipolar current can be through the laparoscopic instrument 218 (connected to the cutter wire 206) and the other pole can be through the cup portion 202.

In at least one embodiment, the shorter cutter 206 can be held between the grooves 208, 210 by a small ball (not shown) at a distal end of the cutter 206. The ball can help the cutter 206 slide around the circumference of the cup portion 202 but also prevents the entire cutter 206 from being pulled out from between the grooves 208, 210 as the laparoscopic instrument 218 pulls the cutter 206. Once the cutter 206 has traversed the entire circumference of the cup portion 202, a break or opening (not shown) between the grooves 208, 210 can allow the ball to be pulled out from the cup portion 202 and into the laparoscopic instrument 218 for removal. This ball configuration can be used with bipolar or monopolar applications. In bipolar applications, a small metal lining inside of the grooves 208, 210 can electrically connect the cup portion 202 to the ball (which is electrically connected to the laparoscopic instrument 218).

The uterine manipulator 10, 300, 400, or at least one or more components of the uterine manipulator 10, 300, can be used with orifice-assisted small incision surgeries (OASIS). In such surgeries, instrumentation can be inserted through a patient's belly button as well as the patient's vagina 110. The optical axis (e.g., of a laparoscope inserted through the belly button) can be decoupled from the operative axis (e.g., of a surgical tool inserted through the vagina 110). The uterine manipulator 10, 300 can include an extension tool to assist with OASIS procedures.

Figure 23:
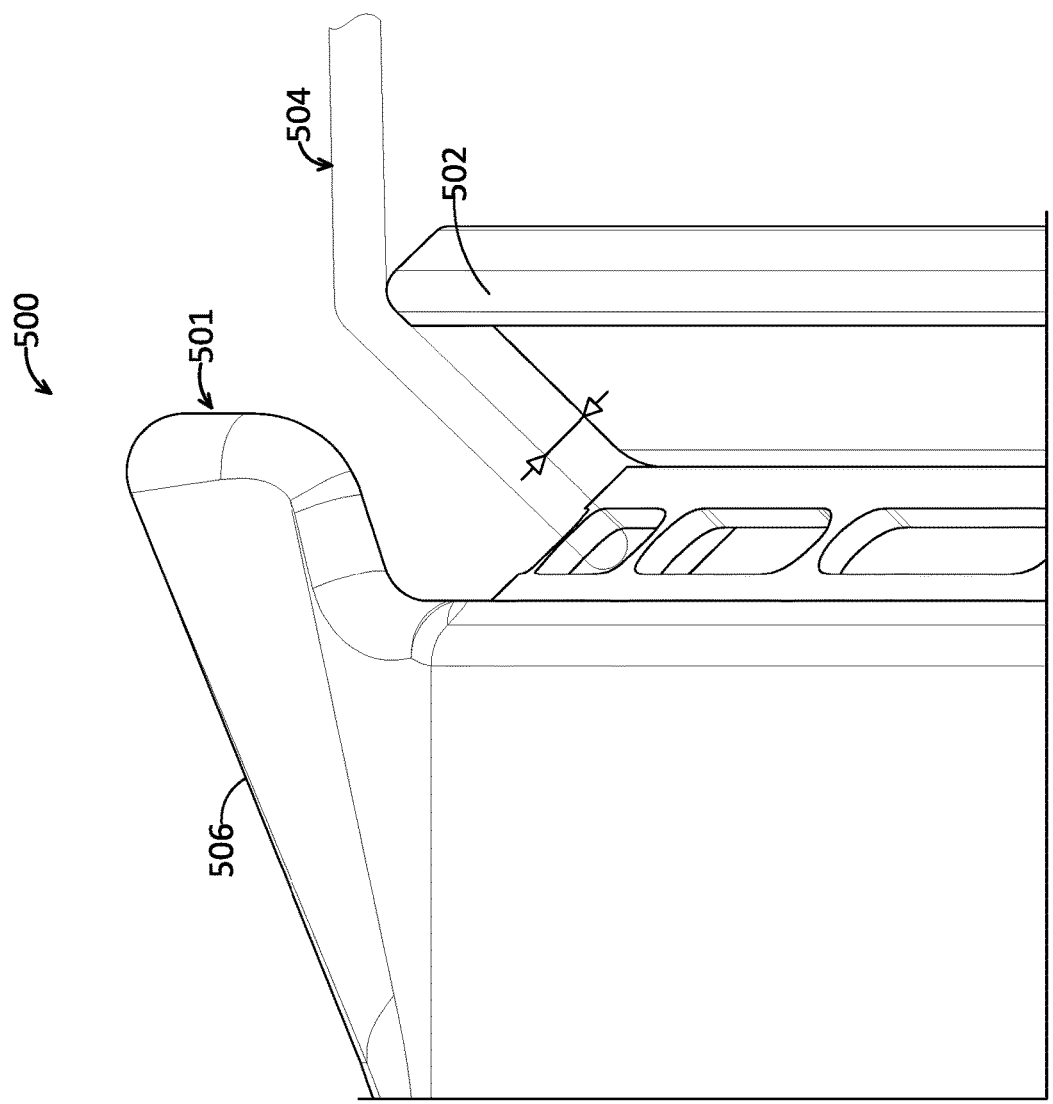
FIG. 23 illustrates a partial side view of a cutting assembly in accordance with the present disclosure.
Figure 24:
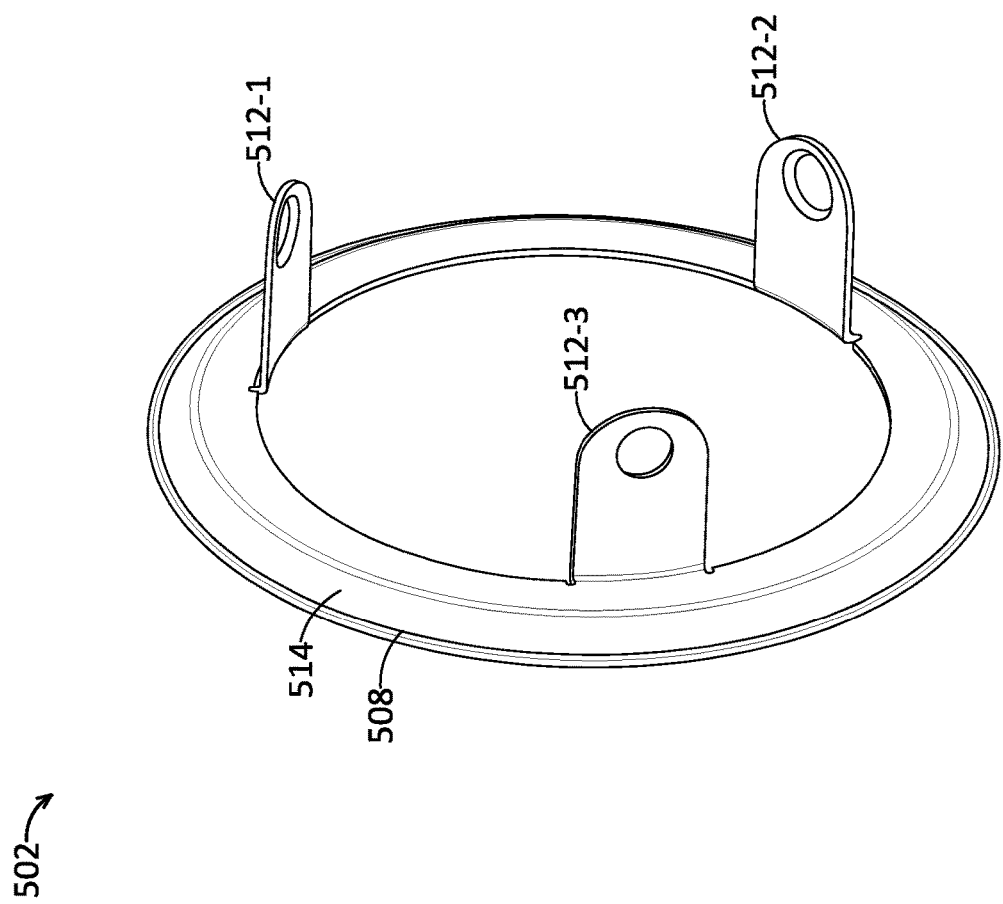
FIG. 24 illustrates a perspective view of a cap of the cutting assembly of FIG. 1.
Figure 25:
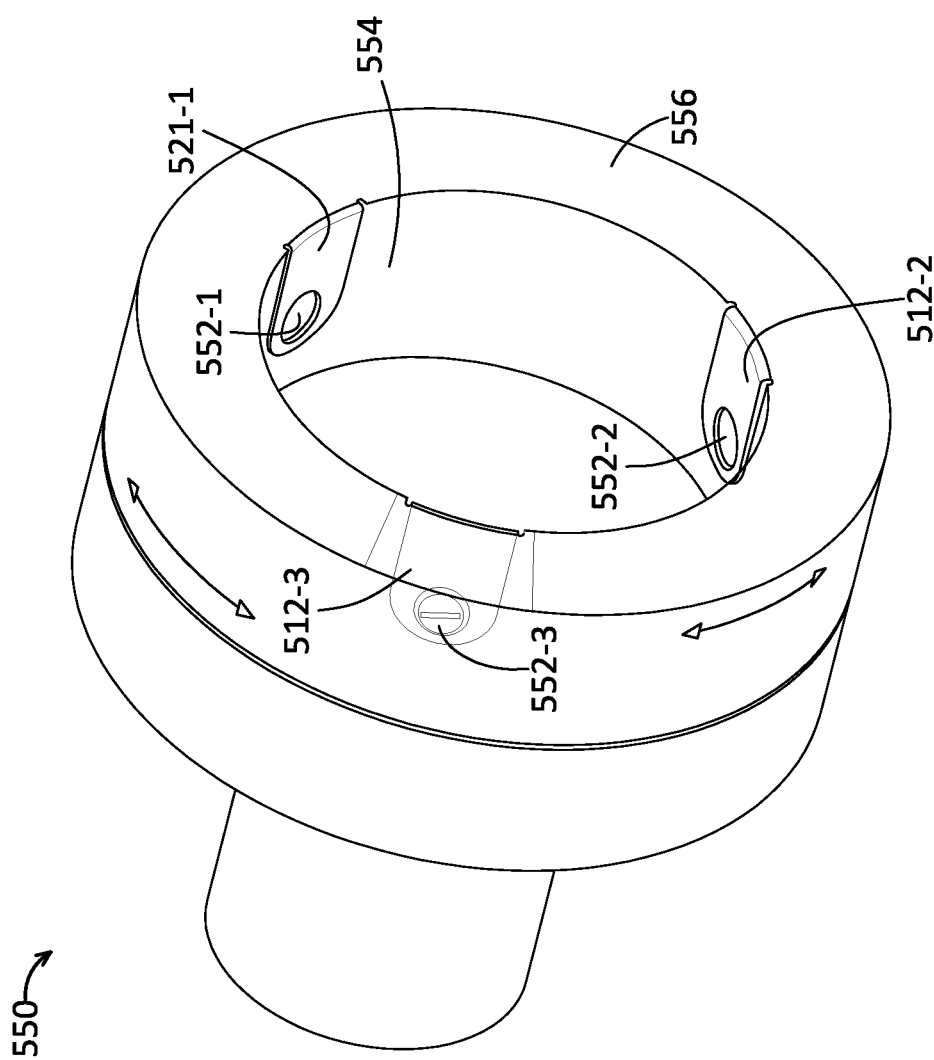
FIG. 25 illustrates a perspective view of a cutting assembly in accordance with the present disclosure.

FIGS. 23-25 illustrate an embodiment of a cutting head that is suitably configured for use with the uterine manipulators disclosed herein, or other uterine manipulators or other medical devices that utilize, or can be modified to utilize, an electrosurgical cutter. It will also be appreciated by those of skill in the art that the disclosed cutting head can be used in a variety of other procedures other than procedures separating the uterus from the vagina, such as bowel resections, gastric bypass procedures and any other procedure that requires separation of biological structures having a tubular or ring shaped component to be cut.

For purposes of illustration, and not limitation, FIG. 23 illustrates a partial side view of a cutting assembly 500 in accordance with the present disclosure. The cup 506 can be configured to be positioned at a juncture between a patient's cervix and vagina. The cutting assembly 500 can include a cutting wire 504. As illustrated in FIG. 23, the cutting wire 504 can pass through an aperture of the cup 506. The cap 502 can include an electrically insulating material disposed thereon (e.g., parylene, or other suitable material). The cutting wire 504 can contact (rest against) the electrically insulating material on the cap 502. The cutting assembly 500 can include a projection 501 that initially pushes the cutting wire 504 through the tissue when the cup 506 is positioned at the juncture between the cervix and the vagina.

The cutting wire 504 can be used to cut the vagina without electrical current ("cold") or with an electrical current ("hot"), based on surgeon preference. Different operations can be conducted based on monopolar or bipolar configurations. Power during monopolar operation can be relatively high, such as about 100 watts. As the cutting assembly 500 rotates about the shaft 406, the cutting wire 504 follows a substantially circular path thereby separating a patient's uterus and cervix from the vagina.

FIG. 24 illustrates a perspective view of a cap 502 of the cutting assembly 500 of FIG. 23. The cap 502 can include a base 514 and an electrically insulating (e.g., plastic, parylene) coating 508. The base 514 can include an electrically conductive material, such as a stainless steel foil. The electrically insulating coating 508 can be bonded to a surface of the base 514. The base 514 can include one or more tabs 512-1, 512-2, and 512-3 for coupling the cap 502 to an interior surface of the cup 506 as discussed further in association with FIG. 25 below. The tabs 512-1, 512-2, and 512-3 can include an aperture through which a fastener (e.g., a screw) can pass.

FIG. 25 illustrates a perspective view of a cutting assembly 550 of a uterine manipulator in accordance with the present disclosure. The cutting assembly 550 can include a cup 554 and a cap 556. The cup 554 and the cap 556 can be analogous to the cup 506 and the cap 502 illustrated in FIG. 23, respectively. Fasteners 552-1, 552-2, and 552-3 can couple the cap 556 to the interior surface of the cup 554 through apertures in the tabs 512-1, 512-2, and 512-3. A cutting wire 504 can be coupled to one of the fasteners, such as the fastener 552-3. For example, the cutting wire 504 can be coupled to an eyelet (not shown). The eyelet can be placed around the fastener 552-3. An electric current can be applied to the cap 556 (e.g., to an electrically conductive material of the base 514 described above). The cap 556 can electrically insulating material to prevent harm and/or injury to a patient from the electric current. The cutting wire 504 can include a looped tip, which can be used to engage a laparoscopic instrument. As indicated by the double-headed arrows in FIG. 25, the cutting assembly 550 can rotate, clockwise and/or counterclockwise. As the cutting assembly 550 rotates, for example about the shaft 406, the cutting wire 504 follows a substantially circular path thereby separating a patient's uterus and cervix from the vagina.

Figure 26B:
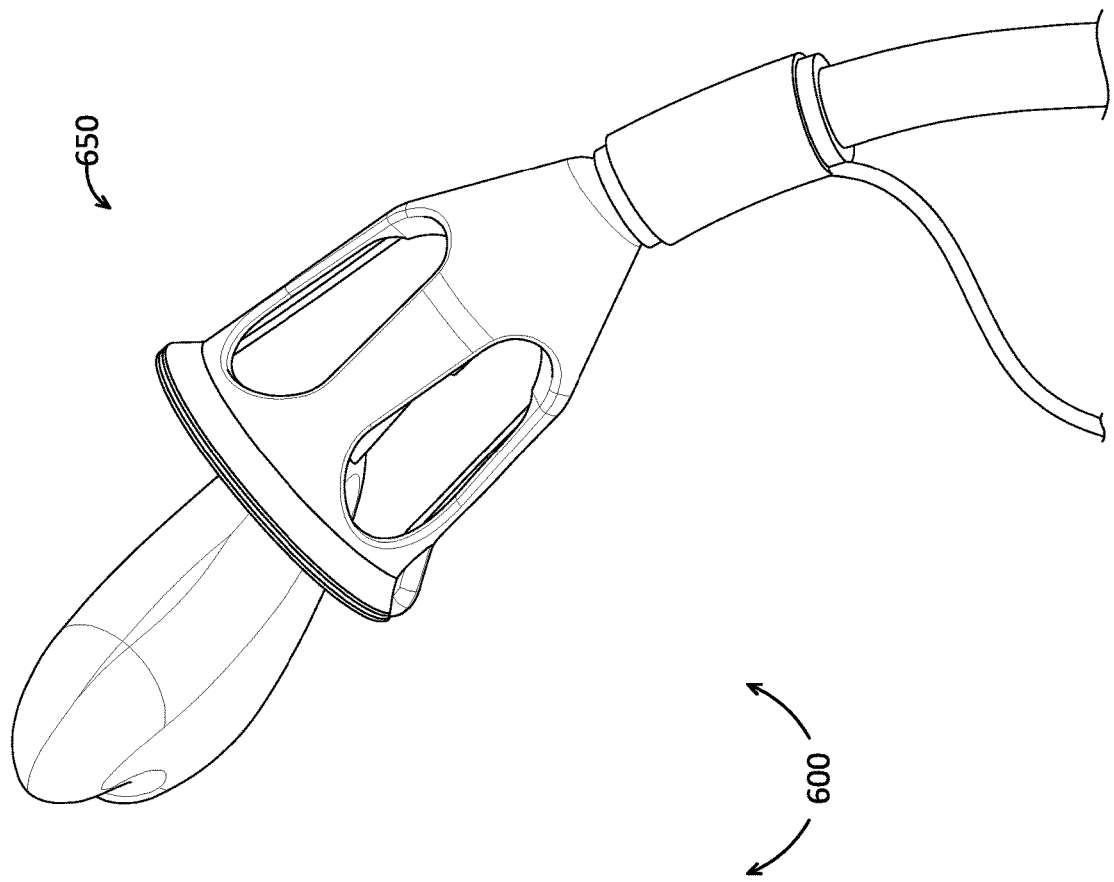
FIG. 26B is an enlarged view of the distal end as presented in FIG. 26A.
Figure 26A:
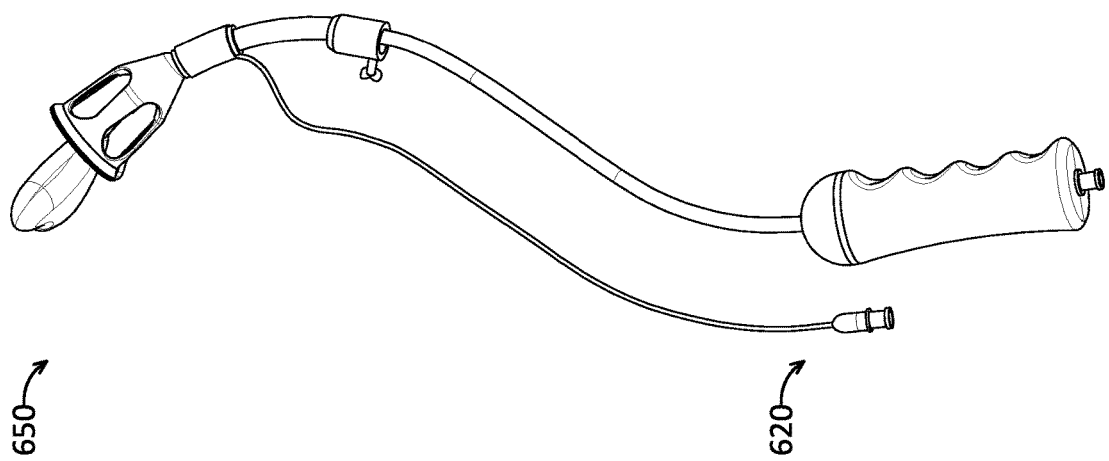
FIG. 26A is a side view of a further representative embodiment of a uterine manipulator in accordance with the present disclosure.

FIG. 26A is a side view of a further representative embodiment of a uterine manipulator in accordance with the present disclosure, and FIG. 26B is an enlarged view of the distal end as presented in FIG. 26A.

Figure 27B:
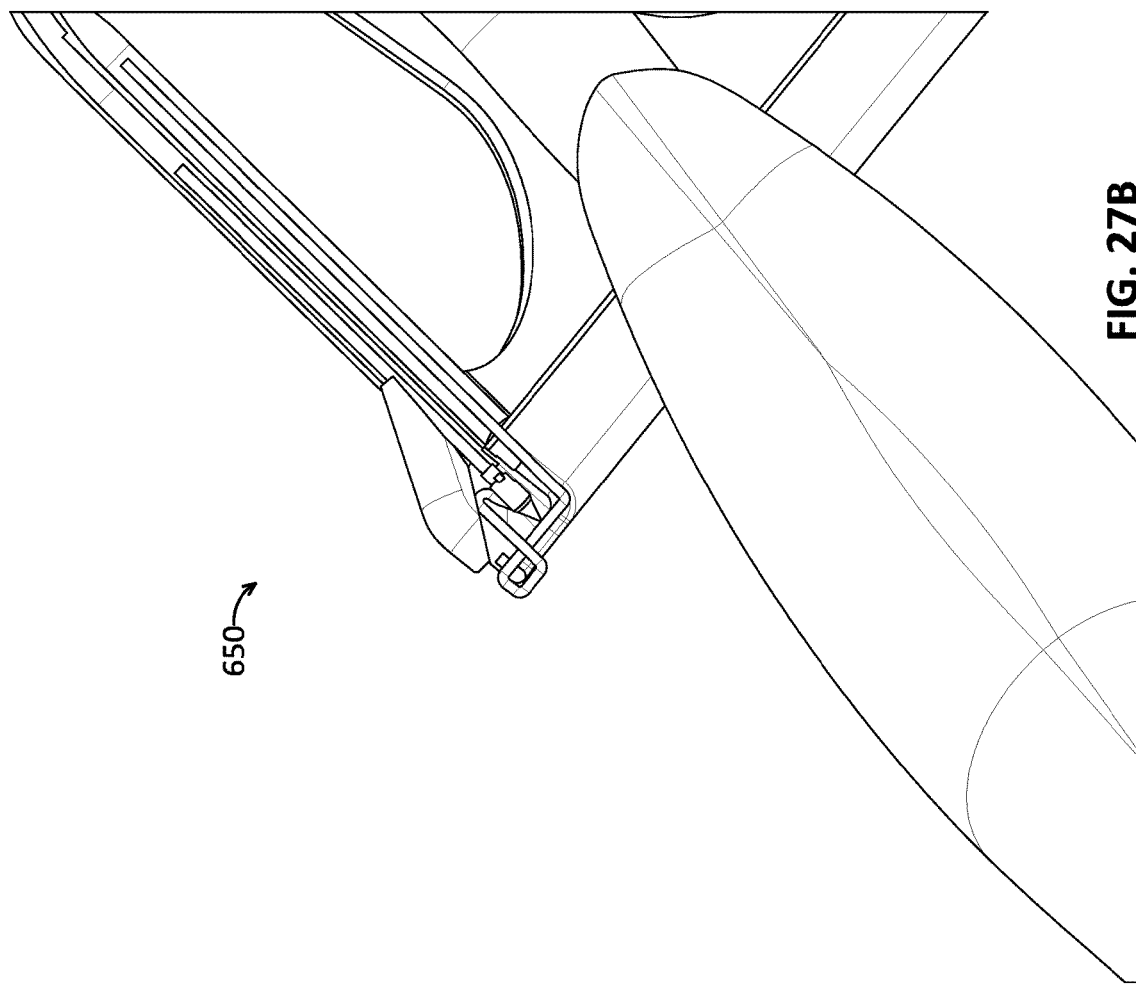
FIG. 27B is an enlarged cut-away view of the distal end as presented in FIG. 27A.
Figure 27A:
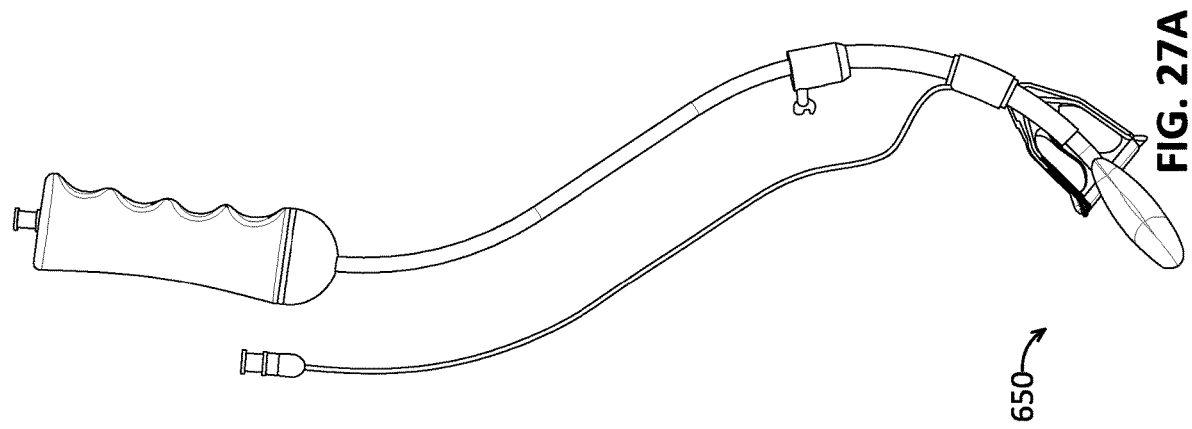
FIG. 27A is a side sectional, or cut-away view of the embodiment of FIGS. 26A-26B.

As illustrated, the uterine manipulator 600 bears a number of similarities to previous embodiments, including a triangular balloon connected to an actuator 620 housed within a distal cup. It will be appreciated that structures other than a triangular balloon can be used. Focusing on the distal end portion 650 of the manipulator 600, FIG. 26B illustrates a side view of a cup that has been configured to provide a bipolar cutting mechanism discussed in further detail below. It will be appreciated that instead of providing a bipolar arrangement including a conductive ring 690 and a return conductor 668, this design can be modified to be a monopolar cutting head by removing those components and making other suitable modifications. FIG. 27A is a side cut away view of the embodiment of FIGS. 26A-26B, wherein FIG. 27B is an enlarged view of the distal end as presented in FIG. 27A showing the location of components discussed in particular detail below.

Figure 28:
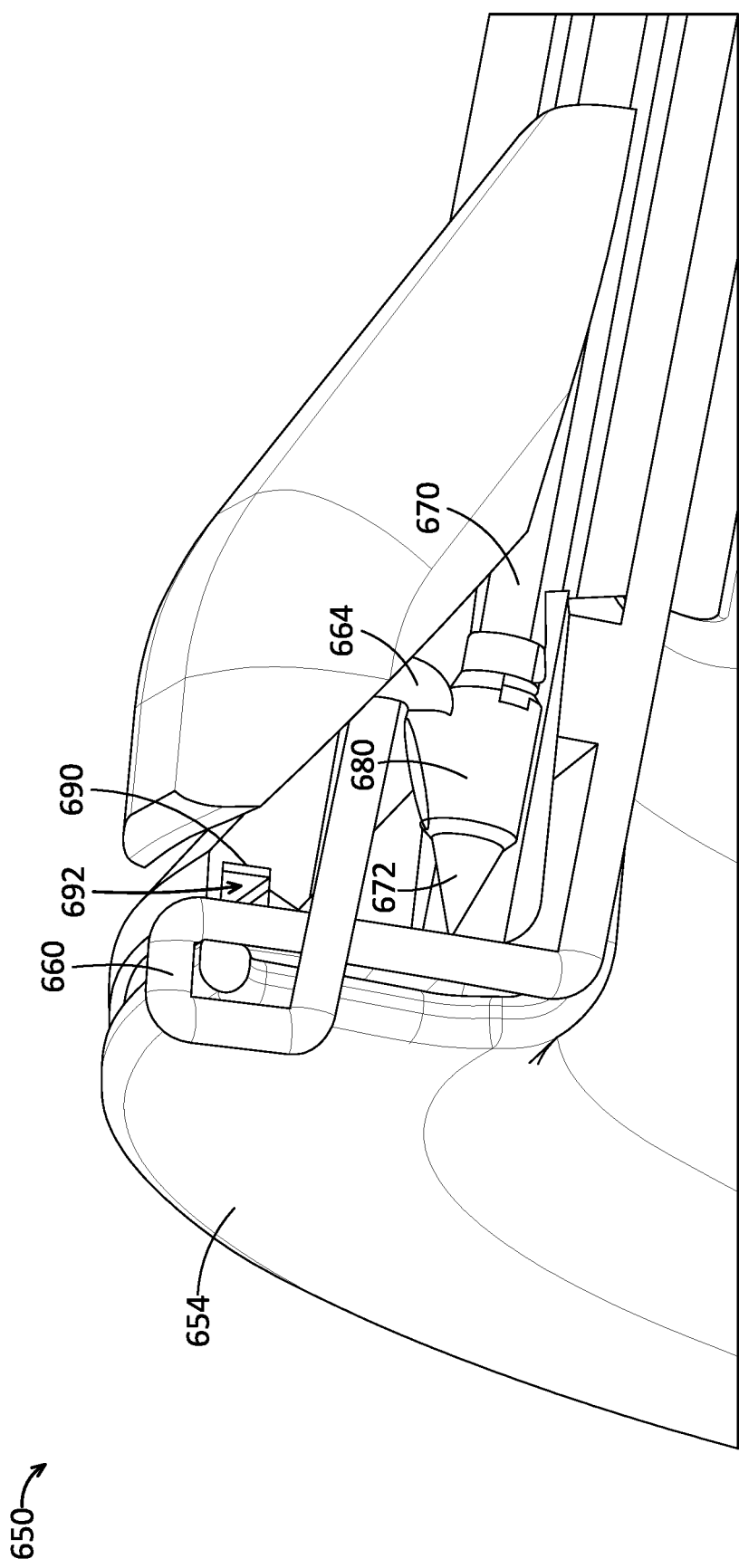
FIG. 28 is a close up cross sectional view of the distal end portion of the uterine manipulator presented in FIG. 26A.

With reference to FIG. 28, a close up cross sectional view of the distal end portion of the uterine manipulator presented in FIG. 26A is presented. Distal end portion 650 includes a cutting head formed by a stationary cup, as opposed to a rotating cup in the preceding embodiment. Procedurally, a hot lead is deployed and advanced by a push wire (e.g., made of stainless steel) through the vaginal wall where it intersects the cervix. The hot wire is externalized so it can be viewed laparoscopically within the abdominal cavity, and where it can be gripped and pulled around (e.g., with forceps or other tool) around the circumference of the distal cup. This avoids the use of a rotating cutting head, and wire that is pre-packed into the distal cutting head is externalized and pulled through as the circumference of the cervix is traversed. Cutting is achieved with the aid of an arc discharge that is present in a toroidal gap (e.g., 692) defined between the hot wire 660 and a conductive ring 690 as the hot wire is pulled around the circumference of the cervix.

Thus, the components illustrated in FIG. 28, and later figures, include the distal cutting head 650 that terminates in an annular, or toroidal, distal cap 654 that preferably includes a coating of insulating material on its proximally and/or distally oriented faces. Beneath the cap within the distal cup is defined an annular trench, or channel, that is configured to receive a conductive ring 690. Ring 690 may be a discrete metallic component or may be metallized on a plastic surface. Ring 690 essentially sits in a trough having a radially outwardly located lip that extends upwardly from the bottom of the trough, and is preferably made from a dielectric material. The radially outwardly located lip cooperates with the circumferential periphery of the distal cap to define an annularly shaped groove therebetween that can permit cutting wire 660 to be drawn through as the device is used to make a 360 degree cut to separate the cervix from the vagina. It will be appreciated that the groove could be slightly less than 360 degrees, if desired, to enhance structural stability. In use, once deployed, the conductive hot lead 660 is pulled radially outwardly through and along the annularly shaped groove. As this happens and power is applied to the hot lead 660 and a return path is defined along ring 690 and conductor 668 (see FIG. 37B), a space always exists between the hot lead 660 and the conductive ring 690. When the applied electric field is sufficiently high, current will flow across the gap 692 from the wire 660 to the ring 690. In the process of doing this, a plasma may or may not be formed locally (depending on the voltage and pulse shape of the applied waveform) which can provide enhanced benefits of reactive oxygen species (ROS) and the like, as well as generally providing the benefits of electrocautery effects to minimize bleeding from the vaginal wall and the severed cervix/uterus.

As illustrated, conductor 660 terminates in a cuff 680 that is in turn engaged by a distal tip 672 of a push rod 670. End cap 654 defines an elongate opening therein that is disposed along a radial direction. The elongate opening is configured to permit the push rod 670 to pass through it, carrying the cuff 680 and a distal end 664 of the hot lead or conductor 660. While a proximal end of the hot lead 660 is shown not extending proximally to the proximal end of the device, this is to simplify illustration. In operation, the proximal lead 660 either extends through the proximal end of the device or follows a conductive path through the proximal end of the device 600 where it is connected to a hot lead of a suitable electrosurgical signal generator, or power supply (not shown). Likewise, the lead 668 (FIG. 37B) also extends through the proximal portion of the device 600 and is electrically coupled to a return terminal of the signal generator/power supply to complete the bipolar circuit, and avoiding the need for a grounding pad, thereby minimizing the amount of electrical energy directed through a patient. Likewise, although not specifically illustrated in the drawings, the push rod 670 also extends proximally to an actuator, not shown, to permit it to be moved distally and proximally with respect to the device to deploy the hot wire.

Figure 29C:
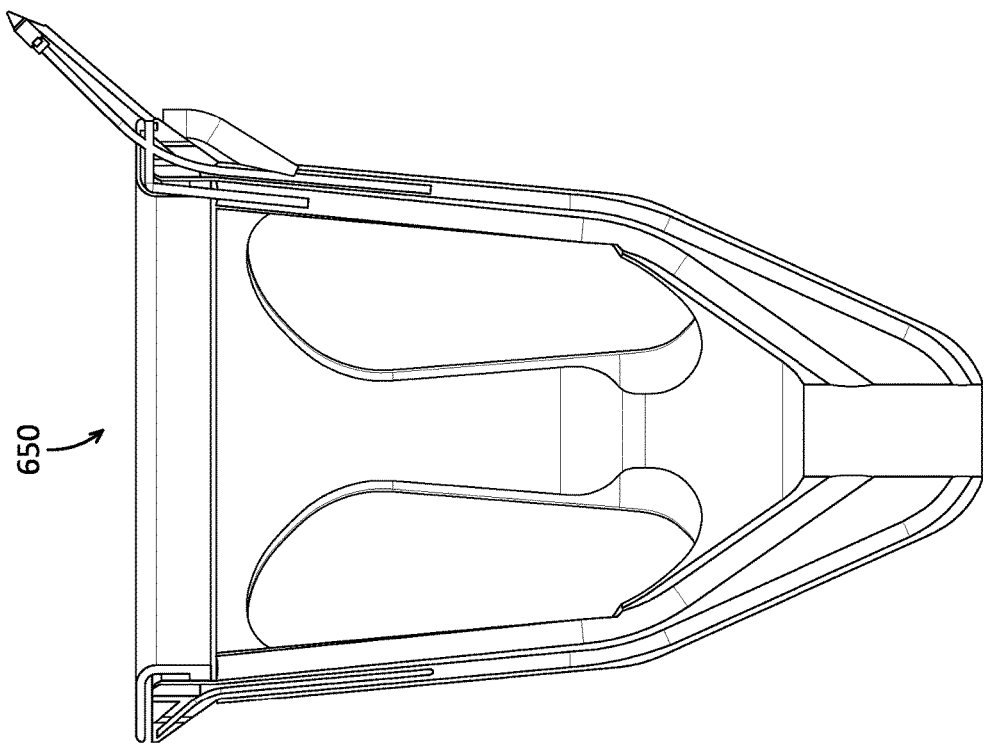
FIGS. 29A, 29B and 29C are a partial section isometric end view, a partial side section view and a full section view of the distal end portion of the uterine manipulator presented in FIG. 26A with the cutting wire partially deployed.
Figure 29A:
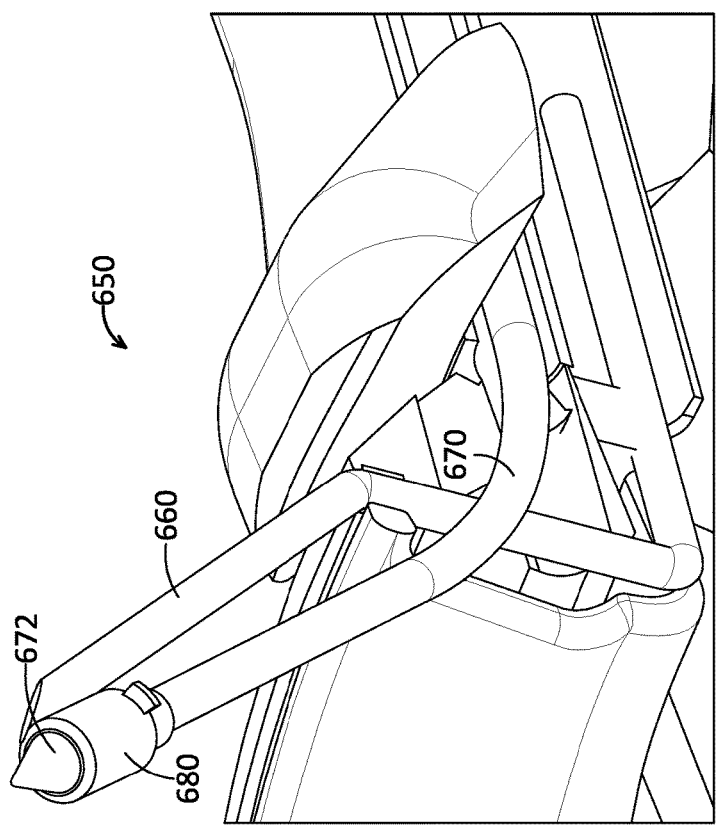
Figure 29B:
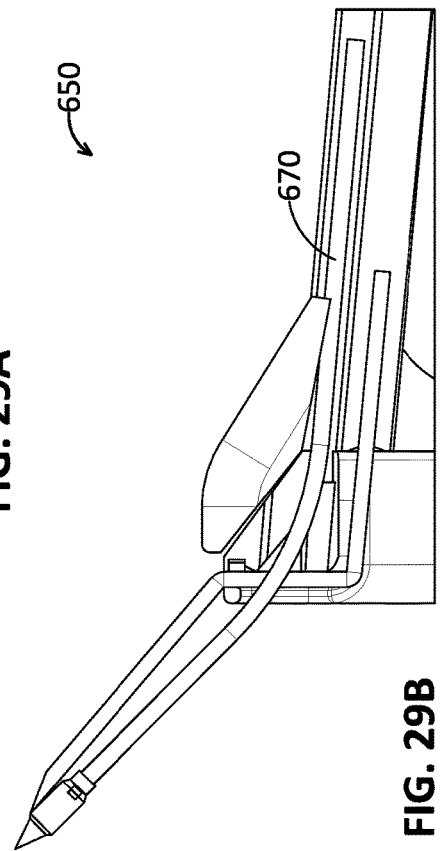

FIGS. 29A, 29B and 29C are a partial section isometric end view, a partial side section view and a full section view of the distal end portion of the uterine manipulator presented in FIG. 26A with the cutting wire partially deployed.

As illustrated in FIG. 29A, the hot wire 660 can be folded in and/or doubled over along the path of the annular gap 692, but preferably located radially inwardly. In operation, FIG. 28 shows the hot wire 660 in a pre-deployed condition, wherein the hot wire is located, or wrapped inside of, the annular gap, and extends radially outwardly from the gap, and wrapped over the radially outwardly solid portion of the end cap 654 (shown in FIGS. 39A-39B) that is defined in part by the radially oriented opening through the end cap. The hot wire 660 then wraps proximally and is received by the cuff 680, which is removably attached to the distal tip 672 of the push rod 670. The push rod 670 (which may be made from stainless steel, for example) is then advanced distally out of the radially oriented gap defined through the end cap 654, pulling along the distal end 664 of the hot lead 660 through the gap 692. As illustrated, the push rod 670 can have a pre-formed curvature that causes it to bend radially outwardly, to pierce tissue near the cervix and pass radially outwardly into the abdominal cavity. While surrounding tissue is not illustrated, it will be appreciated that when the wire 660 has been pushed through the tissue into the abdominal cavity by the push rod 670, it will become visible to a surgeon that is viewing within the abdominal cavity after insufflation using an endoscope and a lighting device through a trocar.

Figure 30C:
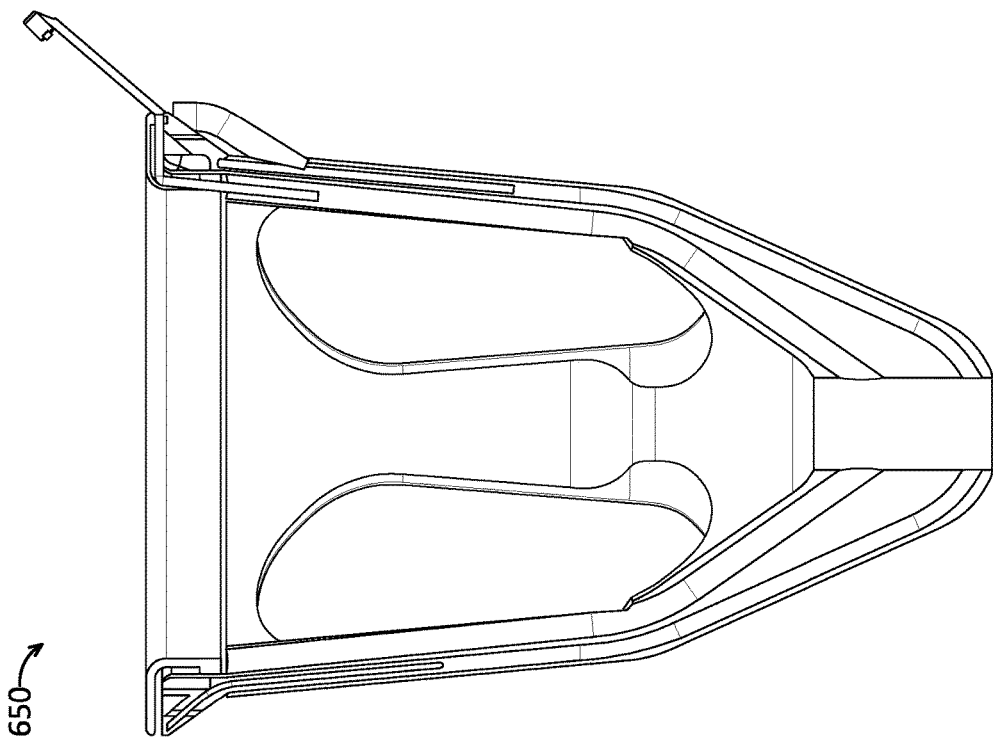
FIGS. 30A, 30B and 30C are a partial section isometric end view, a partial side section view and a full section view of the distal end portion of the uterine manipulator presented in FIG. 26A with the cutting wire partially deployed and the push wire retracted into the device after advancing the hot lead through tissue.
Figure 30A:
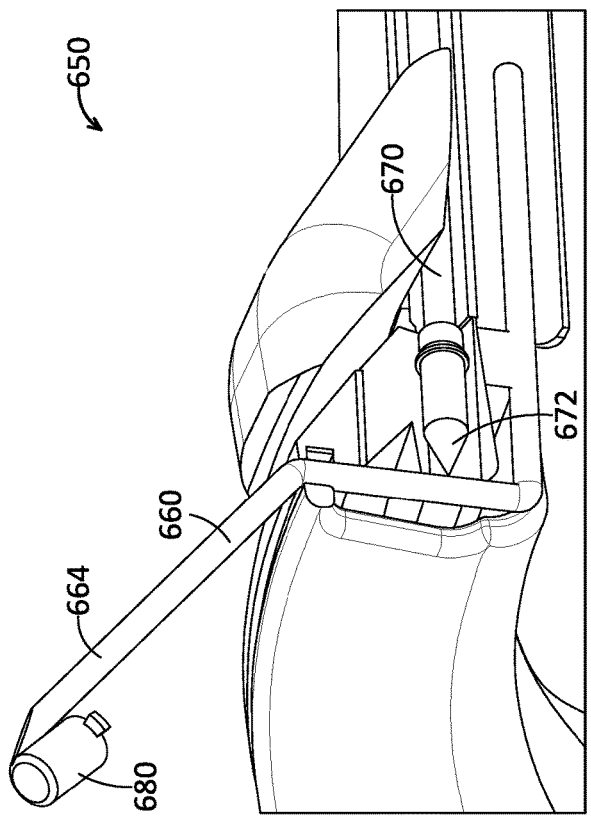
Figure 30B:
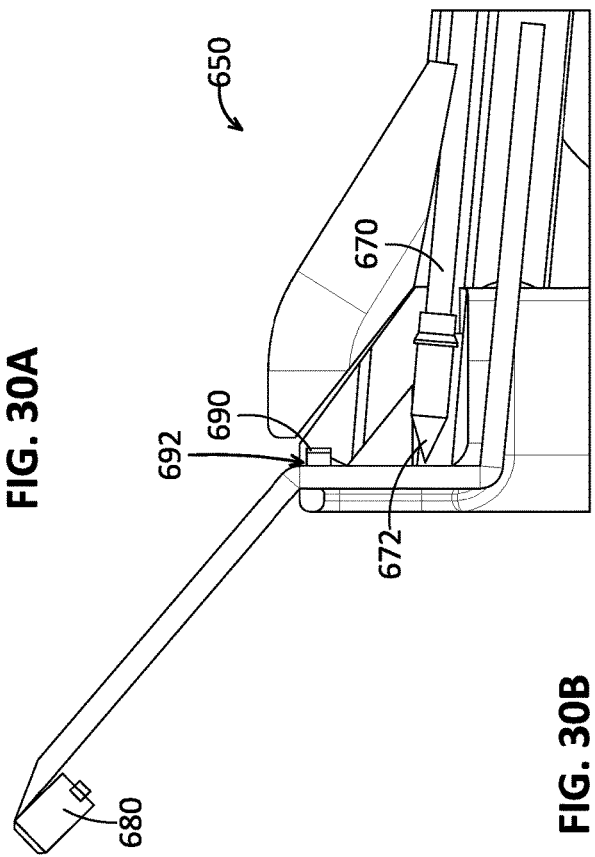

FIGS. 30A, 30B and 30C are a partial section isometric end view, a partial side section view and a full section view of the distal end portion of the uterine manipulator presented in FIG. 26A with the cutting wire partially deployed and the push wire retracted into the device after advancing the hot lead through tissue.

Figure 31:
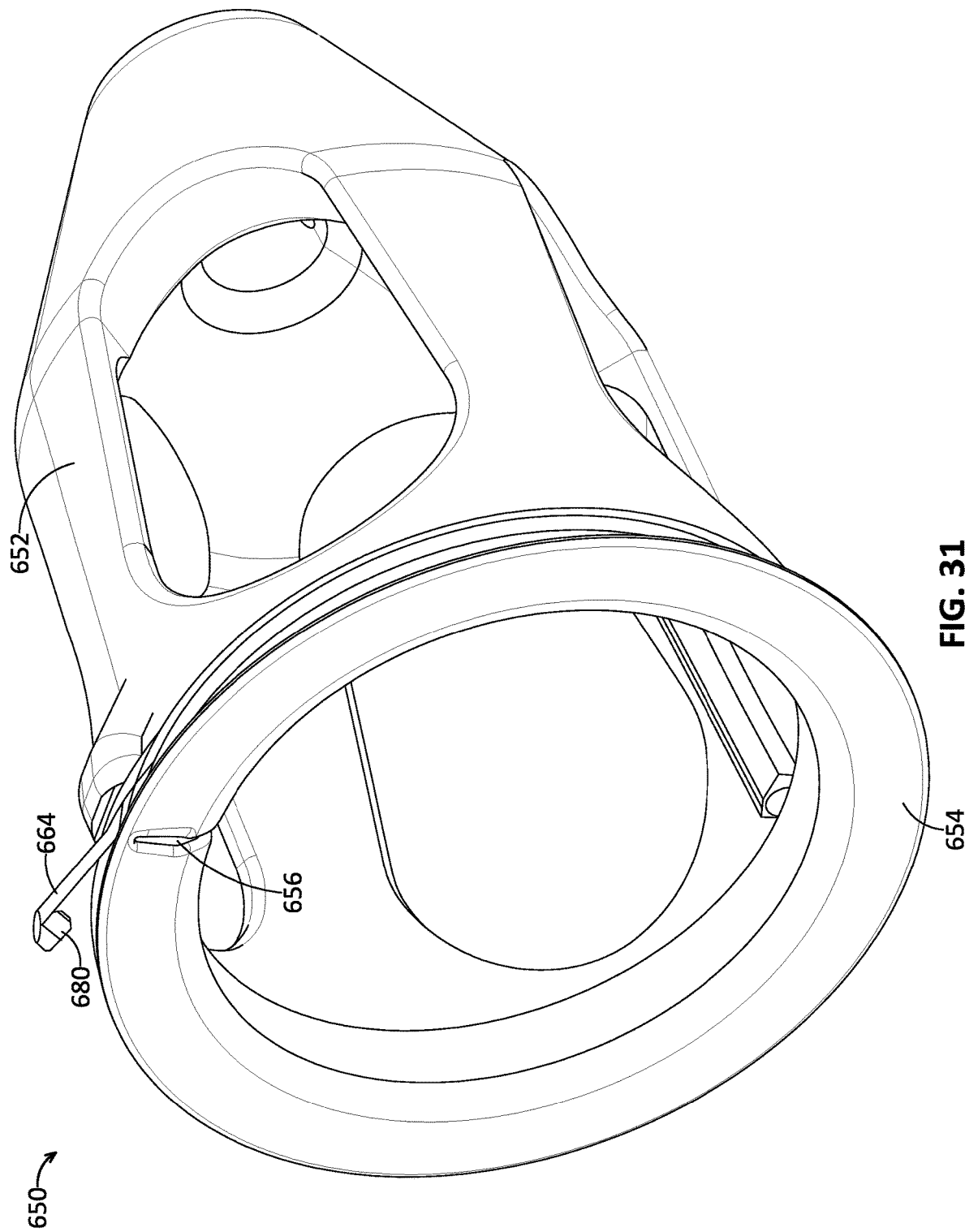
FIG. 31 is an isometric end view of the distal end portion of the uterine manipulator presented in FIG. 26A with the hot lead partially deployed as in FIGS. 30A, 30B and 30C.

FIGS. 30A-30C illustrate the hot wire lead 660 and cuff 680 left in a position that is externalized in an abdominal cavity (without illustrating surrounding tissue for clarity). The push rod 670 is withdrawn back into device 600. This permits a surgeon to then grip the cuff 680 (which may be made from insulating material or with an insulating coating) to then pull the wire around the circumference of the annular gap, either cold (without applied electrical power), or hot (with applied electrical power). FIG. 31 is an isometric end view of the distal end portion of the uterine manipulator presented in FIG. 26A with the hot lead partially deployed as in FIGS. 30A, 30B and 30C prior to being gripped by a surgeon to cut tissue along a circumferential direction. FIG. 31 also illustrates a portion 352 of the cup that can be removable, or permanently attached, to help locate the conductors in place, if desired. This segment is further illustrated in FIGS. 32A-32B which are outer and inner isometric views of a segment of the distal end portion of the uterine manipulator presented in FIG. 26A with the hot lead partially deployed as in FIGS. 30A, 30B and 30C.

Figure 32B:
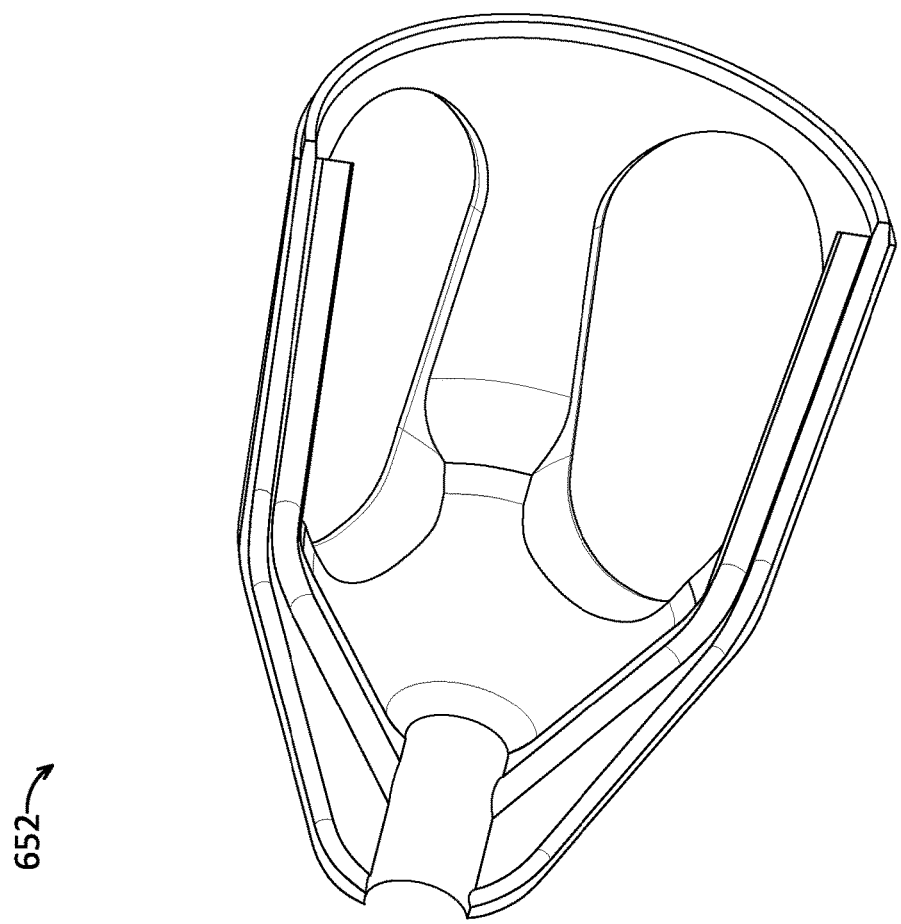
FIGS. 32A-32B are outer and inner isometric views of a segment of the distal end portion of the uterine manipulator presented in FIG. 26A with the hot lead partially deployed as in FIGS. 30A, 30B and 30C.
Figure 32A:
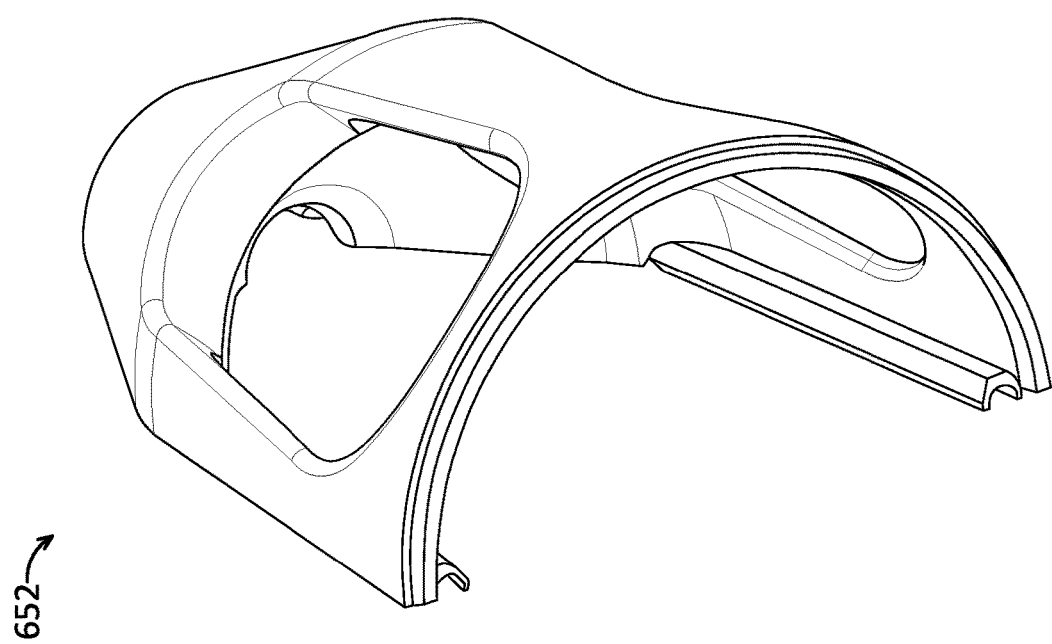
Figure 33B:
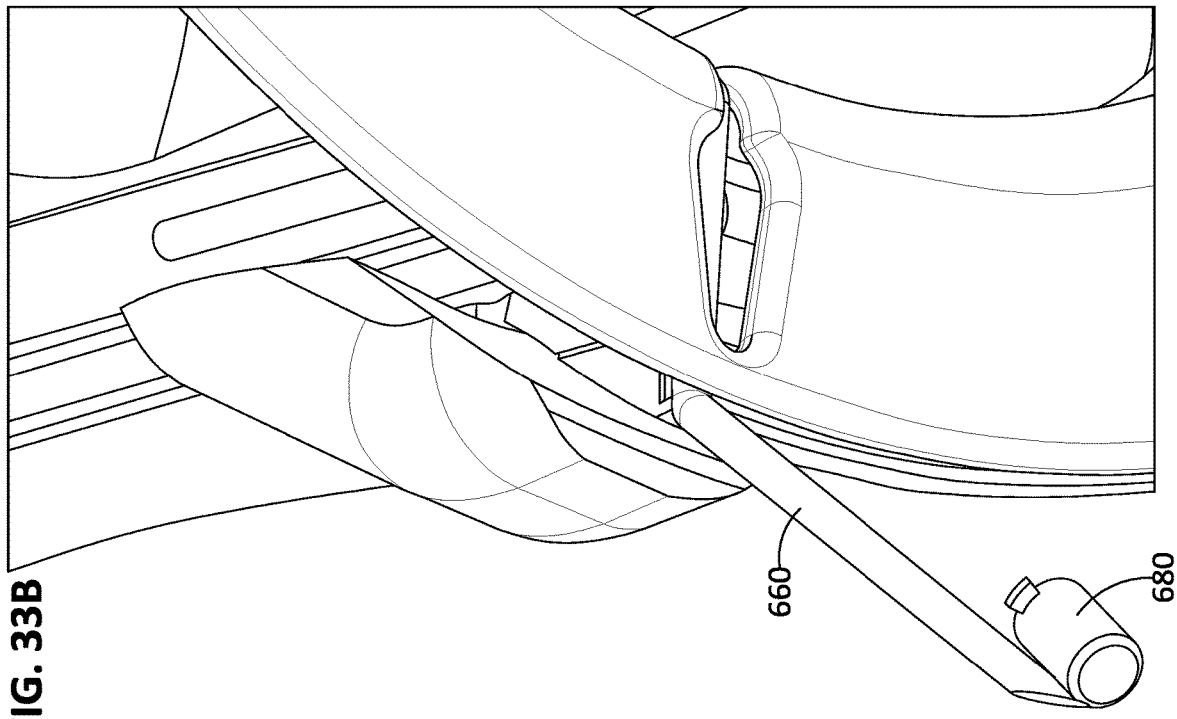
FIGS. 33A-33B are outer and inner isometric views of the distal end portion of the uterine manipulator presented in FIG. 26A with the portion illustrated in FIGS. 32A-32B removed with the hot lead partially deployed as in FIGS. 30A, 30B and 30C.
Figure 33A:
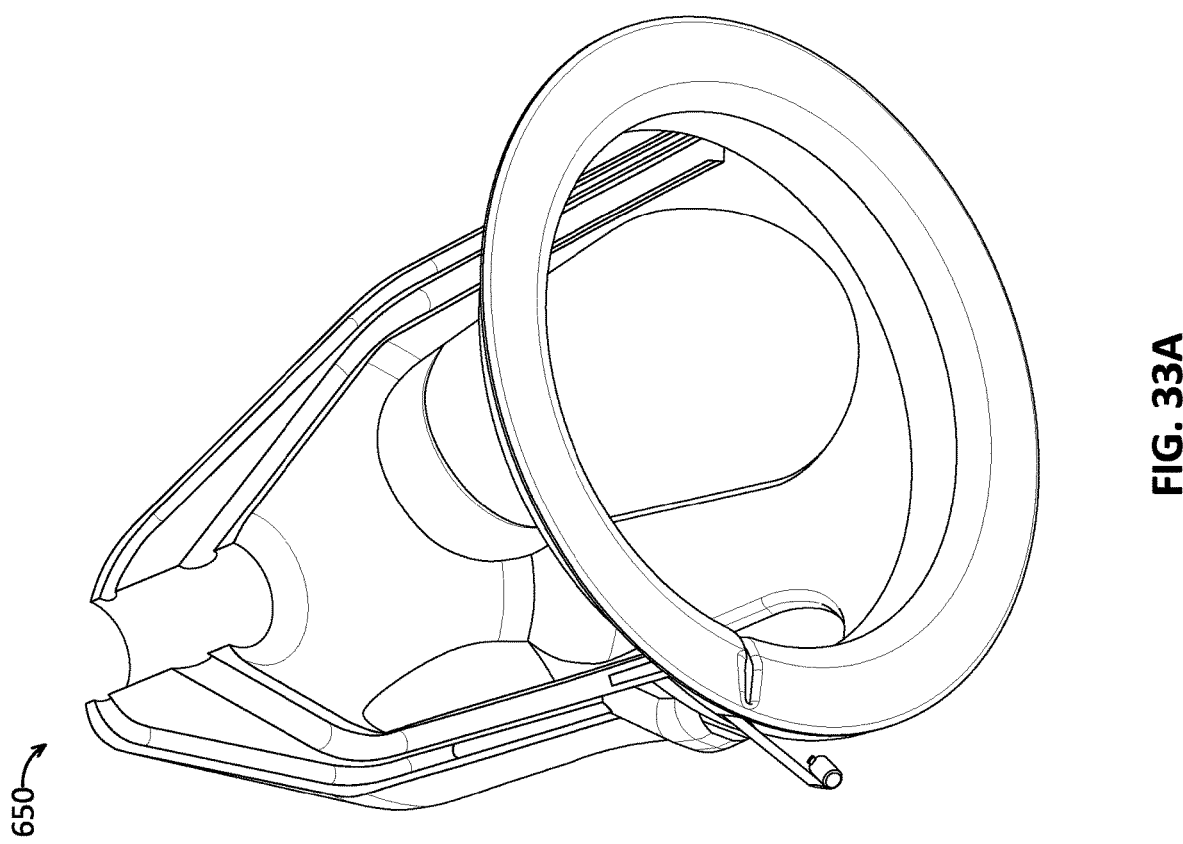
Figure 34B:
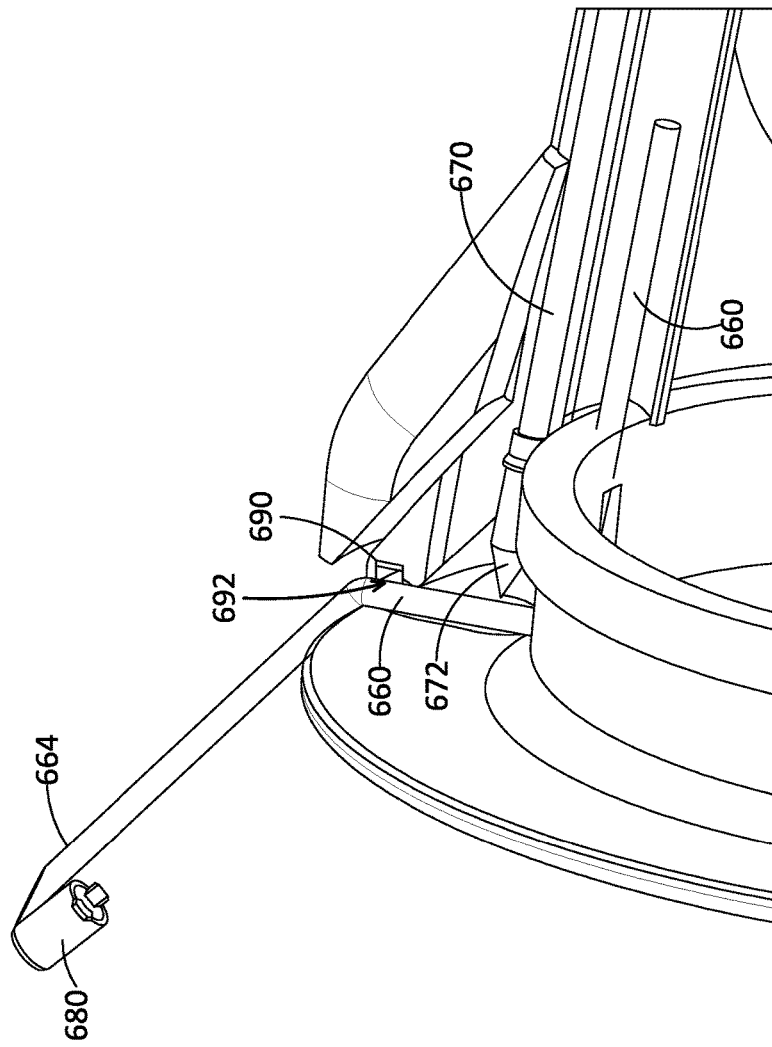
FIGS. 34A-34B are upwardly directed isometric and side cutaway isometric close up views of segments of the distal end portion of the uterine manipulator presented in FIG. 26A with the portion illustrated in FIGS. 32A-32B removed with the hot lead partially deployed as in FIGS. 300A, 30B and 30C.
Figure 34A:
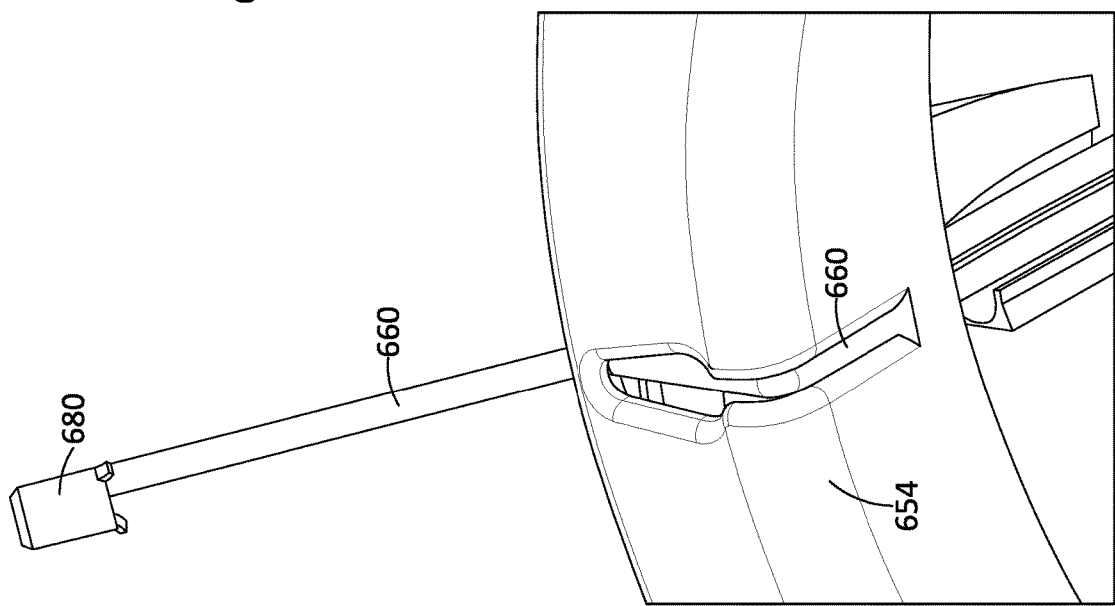

FIGS. 33A-33B are outer and inner isometric views of the distal end portion 650 of the uterine manipulator 600 presented in FIG. 26A with the portion illustrated in FIGS. 32A-32B removed with the hot lead 660 partially deployed as in FIGS. 30A, 30B and 30C to illustrate relative placement of components. Similarly, FIGS. 34A-34B are upwardly directed isometric and side cutaway isometric close up views of segments of the distal end portion 650 of the uterine manipulator 600 presented in FIG. 26A with the portion illustrated in FIGS. 32A-32B removed with the hot lead 660 partially deployed as in FIGS. 30A, 30B and 30C.

Figure 35:
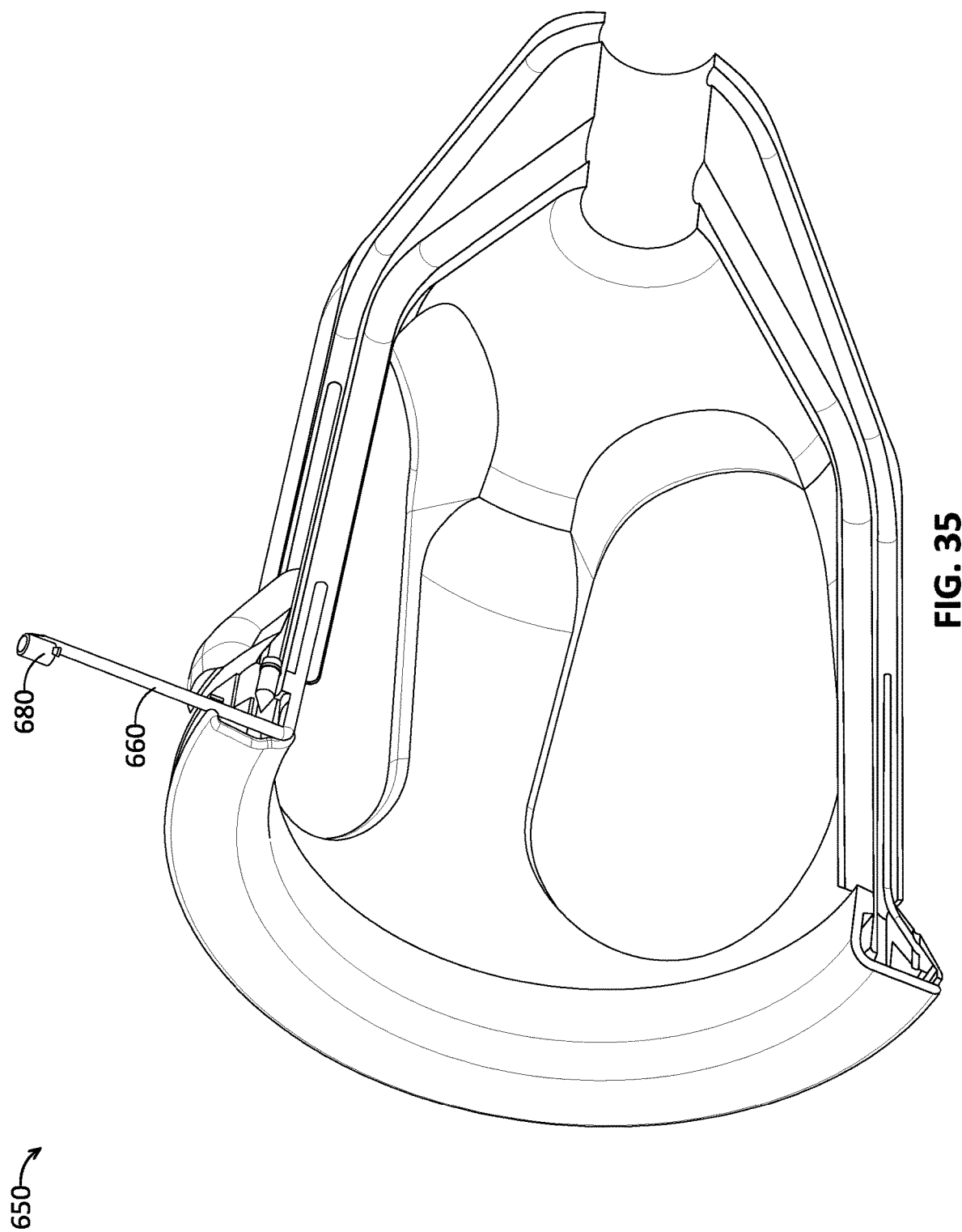
FIG. 35 is an isometric section view of the distal end portion of the uterine manipulator presented in FIG. 26A with the hot lead fully deployed and positioned to cut through tissue to separate a cervix and uterus from a vaginal wall.

Moving along through an illustrative procedure, FIG. 35 is an isometric section view of the distal end portion 650 of the uterine manipulator 600 presented in FIG. 26A with the hot lead 660 fully deployed along a radially outward direction with tension applied thereto at cuff 680 through various means, such as a forceps (not illustrated) and positioned to cut through tissue to separate a cervix and uterus from a vaginal wall. FIG. 36 is a side section view of the distal end portion 650 of the uterine manipulator 600 presented in FIG. 26A with the hot lead 660 fully deployed and positioned to cut through tissue to separate a cervix and uterus from a vaginal wall. FIG. 37A is an isometric close up section view of the distal end portion 650 of the uterine manipulator 600 presented in FIG. 26A with the hot lead 660 fully deployed and positioned to cut through tissue to separate a cervix and uterus from a vaginal wall. FIG. 37B is an isometric close up section view of the distal end portion 650 of the uterine manipulator 600 presented in FIG. 26A showing a cutaway portion of the distal cup opposite the hot lead 660, illustrating a further portion of the conductive ring 690 connected to the further electrical conductor 668 for providing a return path for applied power as described above.

FIG. 38A is a further isometric close up section view of the distal end portion of the uterine manipulator presented in FIG. 26A with the hot lead fully deployed and positioned to cut through tissue to separate a cervix and uterus from a vaginal wall.

Figure 39B:
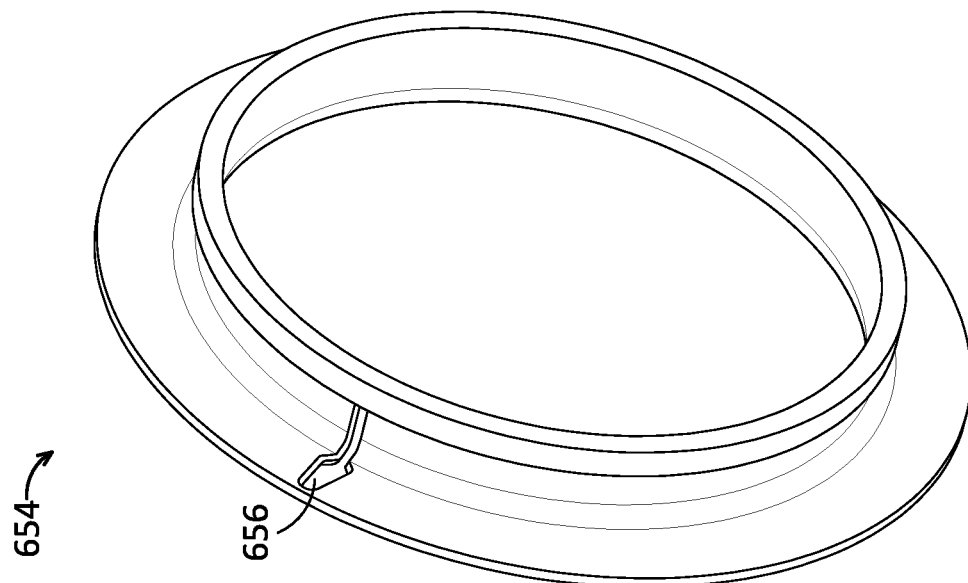
FIGS. 39A-39B illustrate a ring shaped end cap of the uterine manipulator presented in FIG. 26A illustrating an opening therein for accommodating passage of a push wire in accordance with the present disclosure.
Figure 39A:
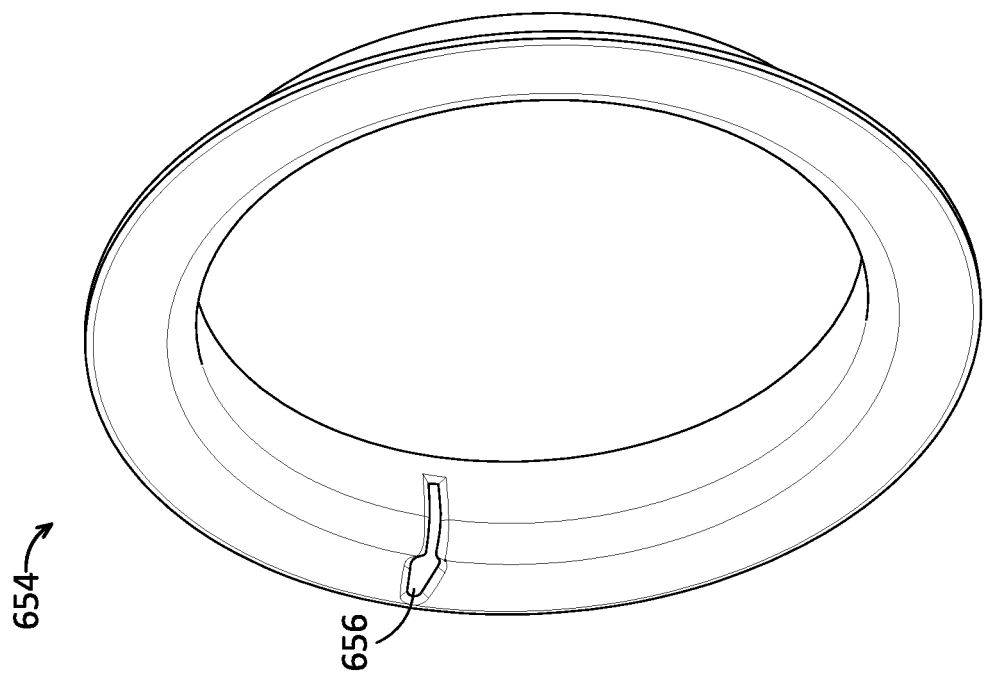

FIG. 38B is a further side close up sectional view of a distal end portion 650 of the uterine manipulator 600 presented in FIG. 26A with the hot lead 660 fully deployed and positioned to cut through tissue to separate a cervix and uterus from a vaginal wall, specifically illustrating a portion of a ring-shaped, or toroidal gap 692 defined between the hot lead 660 and the conductive ring 690 attached to a return conductor 668. FIGS. 39A-39B illustrates the ring shaped end cap 654 of the uterine manipulator presented in FIG. 26A illustrating the opening 656 therein for accommodating passage of a push wire in accordance with the present disclosure.

It will be appreciated the cutting head of FIGS. 28-39 can be suitably combined with any of the features present in the earlier embodiments of the present disclosure. Stated another way, any of the embodiments of FIGS. 1-22 can be modified to include the cutting head of FIGS. 28-39.

The present disclosure has described one or more preferred embodiments. However, it should be appreciated that many equivalents, alternatives, variations, and modifications, aside from those expressly stated, are possible and within the scope of the invention.

What is claimed is:

1. A uterine manipulator, comprising: a shaft including a proximal end, a distal end, and a channel along a longitudinal axis of the shaft; a handle coupled to the proximal end of the shaft; a cutting head attached to the distal end of the shaft adapted to sever a vagina from a cervix and uterus, the cutting head including: a cup coupled to the distal end of the shaft and configured to be positioned at a juncture between the cervix and the vagina, and a cutting wire conforming to and extending around at least a portion of the cup when in a stored position, wherein the cutting wire is configured to follow a substantially circular path when unwound about the longitudinal axis of the shaft; and a push wire slidably disposed within the shaft, the push wire having a distal end portion configured to engage a distal portion of the cutting wire so that when the push wire is advanced distally, the push wire pulls the cutting wire outwardly from the cup.

2. A system comprising the uterine manipulator of claim 1, and a power source coupled to the cutting wire to apply electrical current to the cutting wire.

3. The system of claim 2, wherein the uterine manipulator and power source are configured and arranged to provide monopolar current to a patient.

4. The system of claim 2, wherein the uterine manipulator and power source are configured and arranged to provide bipolar current to a patient.

5. A method of separating a uterus from a vagina of a patient, comprising:
   providing the uterine manipulator of claim 1;
   engaging a cervix of the patient with the cup; and
   sliding the push wire relative to the shaft, thereby deploying the distal portion of the cutting wire through the tissue of the vagina and/or cervix outwardly into an abdominal cavity of the patient.

6. The method of claim 5, further comprising visually locating the distal portion of the cutting wire extending into the abdominal cavity via a laparoscopic procedure.

7. The method of claim 6, further comprising grasping the distal portion of the cutting wire using a second surgical instrument from within the abdominal cavity, and pulling the wire circumferentially around the cervix to sever the vagina from the uterus and/or cervix.

8. The method of claim 7, wherein the severing is accomplished without application of electrical current to the uterine manipulator.

9. The method of claim 7, wherein the severing is accomplished with application of electrical current to the uterine manipulator.

10. The uterine manipulator of claim 1, wherein the distal end portion of the cutting wire comprises a cuff, and the distal end portion of the push wire is configured for being inserted into the cuff to carry the distal portion of the cutting wire outwardly from the cup.

11. The uterine manipulator of claim 10, wherein the distal portion of the push rod comprises a tissue-piercing tip.

12. The uterine manipulator of claim 1, wherein the cup has an annularly shaped groove, and the cutting wire extends around and is seated within at least a portion of the annularly shaped groove of the cup when in the stored position.

13. The uterine manipulator of claim 12, wherein the cutting head further comprises an end cap defining at least part of the annularly shaped groove.

14. The uterine manipulator of claim 13, wherein the push wire is configured to traverse an opening defined through the end cap.

15. The uterine manipulator of claim 14, wherein the distal portion of the cutting wire is housed within the cup, and wherein distal advancement of the push wire carries the cutting wire distally and radially outward from the cup.

16. The uterine manipulator of claim 14, wherein the distal portion of the cutting wire extends outwardly from the annularly shaped groove, and wraps around a radially outwardly solid portion of the end cap and proximally through the opening of the end cap.

17. The uterine manipulator of claim 13, wherein the end cap defines a trough, and the cutting head further comprises a conductive ring disposed within the trough and spaced from the cutting wire, the uterine manipulator further comprising a return path conductor extending along the shaft and coupled to the conductive ring.

18. The uterine manipulator of claim 12, wherein a distal portion of the cutting wire is disposed within and around the annular shaped groove of the cup, and a proximal portion of the cutting wire is disposed within the shaft.

19. The uterine manipulator of claim 1, wherein the distal portion of the push wire has a pre-formed curvature to bend radially outwardly to pierce tissue near the cervix.

* * * * *